(12) United States Patent
Green et al.

(10) Patent No.: US 6,724,419 B1
(45) Date of Patent: Apr. 20, 2004

(54) SYSTEM AND METHOD FOR ACQUIRING IMAGES AT MAXIMUM ACQUISITION RATE WHILE ASYNCHRONOUSLY SEQUENCING MICROSCOPE DEVICES

(75) Inventors: Daniel M. Green, West Chester, PA (US); William Peterson, West Chester, PA (US); Avrum Cohen, Malvern, PA (US); Michael D. Sjaastad, Palo Alto, CA (US); Jeffrey A. Stuckey, Jeffersonville, PA (US)

(73) Assignee: Universal Imaging Corporation, Downingtown, PA (US)

( * ) Notice: Subject to any disclaimer, the term of this patent is extended or adjusted under 35 U.S.C. 154(b) by 737 days.

(21) Appl. No.: 09/638,548

(22) Filed: Aug. 14, 2000

Related U.S. Application Data
(60) Provisional application No. 60/148,819, filed on Aug. 13, 1999.

(51) Int. Cl.$^7$ ............................................. H04N 7/18
(52) U.S. Cl. ............................................. 348/79
(58) Field of Search .................... 348/61, 79, 80; 250/311; 396/432; H04N 7/18

(56) References Cited

U.S. PATENT DOCUMENTS
5,233,197 A  8/1993  Bowman et al. ......... 250/461.1
6,633,331 B1 * 10/2003 Potter et al. .................. 348/80

* cited by examiner

*Primary Examiner*—Young Lee
(74) *Attorney, Agent, or Firm*—Elman Technology Law, P.C.

(57) ABSTRACT

The invention provides an automated microscope system, a computer program product in a computer readable medium and a method for acquiring images at substantially the maximum acquisition rate of a camera while and as devices external to the camera, which vary various parameters of the acquired images, operate asynchronously with the camera so as to allow the acquired images to be displayed as a sequence that shows continuous variation in the acquisition parameters.

26 Claims, 23 Drawing Sheets

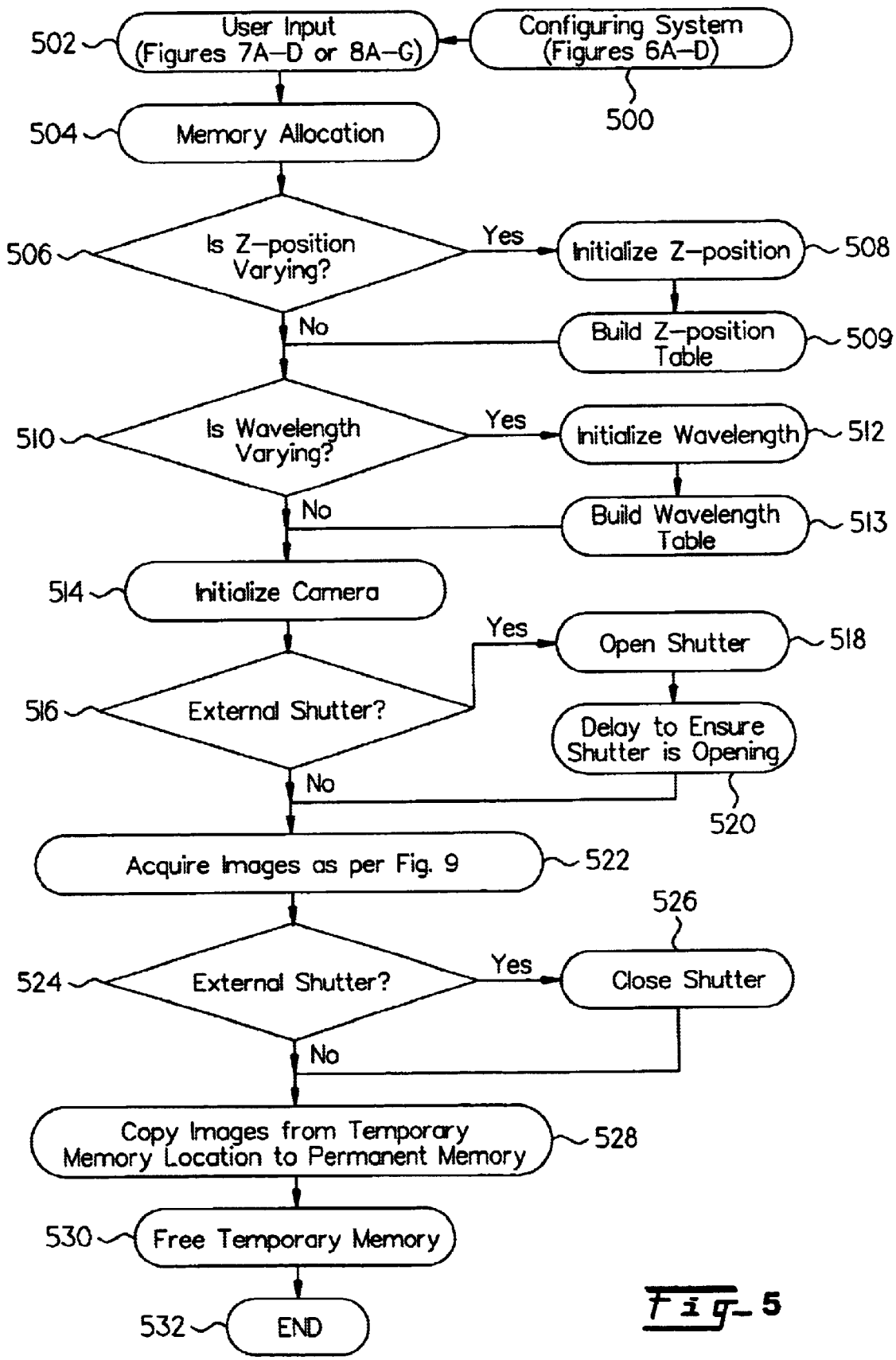

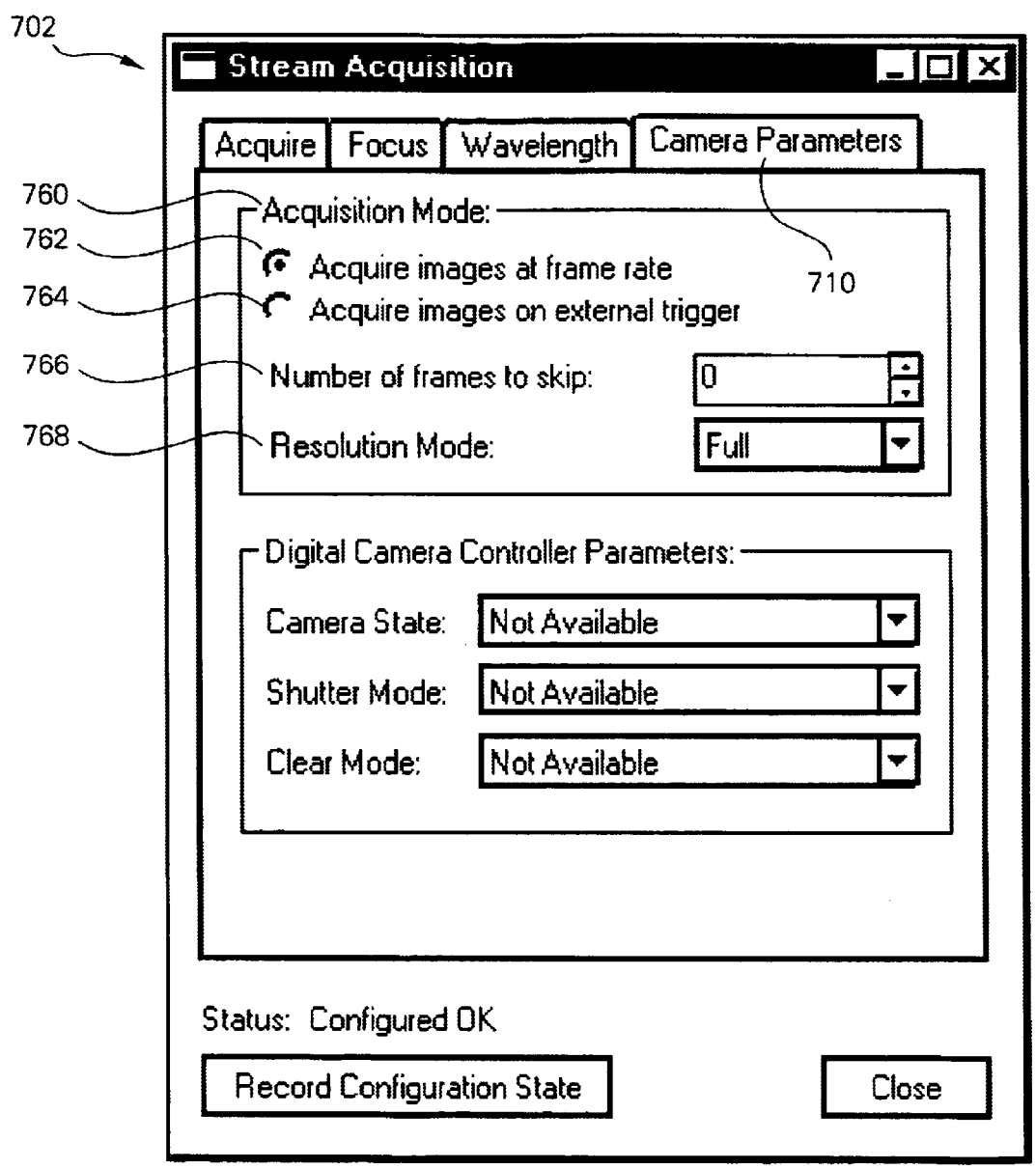
Fig_7D

SYSTEM AND METHOD FOR ACQUIRING IMAGES AT MAXIMUM ACQUISITION RATE WHILE ASYNCHRONOUSLY SEQUENCING MICROSCOPE DEVICES

CROSS-REFERENCE TO RELATED APPLICATION

This application claims the benefit of U.S. Provisional Application No. 60/148,819, filed Aug. 13, 1999.

BACKGROUND OF THE INVENTION

1. Field of the Invention

This invention relates to the field of acquiring images using an automated optical microscope system that includes a camera and particularly, to a method and system for acquiring images as devices external to the camera, which alter various parameters of the acquired images, operate asynchronously with the camera so as to allow such images to be displayed as a sequence that shows continuous variation in the acquisition parameters.

2. Discussion of the Prior Art

Performing research on living cells demands the use of an automated microscope system controlled by application software. With particular reference to the fluorescence microscopy of cells and tissues, various methods for imaging fluorescently-stained cells in a microscope and for extracting information about the spatial and temporal changes occurring in these cells are well known in the art. An article by Taylor, et al. in American Scientist 80 (1992), p. 322–335 describes many of these methods and their applications. Such methods have been particularly designed for the preparation of fluorescent reporter molecules so as to yield, after processing and analysis, spatial and temporal resolution imaging measurements of the distribution, the amount and the biochemical environment of these molecules in living cells.

As regards automating microscope systems, it is well known in the art that automated microscope systems may arrange any one of a wide variety of cameras and an array of hardware components into various instrumentation configurations, depending on the specialized research task at hand. A standard reference, especially useful for an exposition of automated optical microscopy hardware, hardware systems and system integration, is Video Microscopy, 2d Ed., 1997 by Inoué and Spring, which is incorporated herein by reference, especially Chapter 5. More generally descriptive of automated image acquisition and three-dimensional image visualization is John Russ's, The Image Processing Handbook, 3d Ed., 1999, pp:1–86, 617–688 and references therein.

Also well known is that an application software package may supplement and overlay a particular instrumentation configuration by controlling and specifying the sequence, way, and functionalities of image acquiring and processing that the instrumentation system performs. The acquiring and processing operations that the software package is called upon to do depends, again, on the specialized research task at hand. The chapter titled "A High-Resolution Multimode Digital Microscope System" by Salmon et al. in Methods in Cell Biology, vol. 56, ed. by Sluder & Wolf, 1998, pp:185–215 discusses the design of a hardware system, including the microscope, camera, and Z-axis focus device of an automated optical microscope as well as application software for automating the microscope and controlling the camera.

Existing application software for automating a microscope system can direct and control a host of operations, including:

image acquisition from Recommended Standards ("RS")-170 video devices, charge-coupled devices, NTSC and PAL video sources;

setting exposure time, gain, analog to digital conversion time, and bits per pixel for camera settings at each emission and/or excitation wavelength;

driving the digitizing of acquired images from an analog to digital converter;

storing acquired images in a variety of formats, such as TIFF, BMP, and other standard file formats;

driving microscope illumination;

providing capability of creating macros from a user-specified sequence of program commands, which are saved and recorded and able to be played back at a single click;

performing certain processes on a group of related images, called a stack, such as aligning images within the stack, rendering a 3-dimensional reconstruction, saving the stack to a disk, enhancing the images, deblurring the images, performing arithmetic operations; and analyzing image parameters, such as ratio imaging the concentration of ions and graphing changes in intensity and in ratios of ion concentration over time.

An example of widely-used, prior application software for automating a microscope system is the Meta Imaging Series™ available from Universal Imaging Corporation, West Chester, Pa., which is a constellation of related application programs, each having a different purpose. For example, a user wanting a general, multipurpose image acquisition and processing application would employ the MetaMorph™ application program; while a user needing to perform ratiometric analysis of intracellular ion measurements would employ MetaFluor™.

Notwithstanding the above list of operations that prior application software can direct an automated microscope system to do, prior application software has not heretofore enabled an automated microscope system to acquire a group of images while and as acquisition parameters, such as the focus position and the emission and/or excitation wavelength, vary so that the acquired group of images can be played back as a sequence that shows continuous change in those parameters. That is, prior application software has not been capable of directing external devices that control image acquisition parameters to operate asychronously with the camera in order to acquire a group of images that may displayed as sequence showing continuous change in system parameters.

Acquiring a group of images asynchronously as a biological event is occurring so that the images can be played back as a sequence displaying continuous change in certain parameters of the microscope system has enormous importance in research with living cells. The importance of the present invention to cell research may be analogized to the importance of time-lapse photography to the study of macroscopic living systems. However, to be clear, the present invention is not merely a method akin to time-lapse photography of images acquired of living structures and processes at the cellular level. Using prior application software for processing images of cellular structures and mechanisms, a researcher is unable to observe a continuous stream of images that show uninterrupted change in system parameters other than time. The present invention allows a researcher to vary parameters, such as the position of the lens objective and the emission and/or excitation wavelength, during image acquisition so that on playback the acquired set of images may display this variability as continuous change. Specific examples of the kind of research that benefits from using the current invention include observing the movement of adhered proteins on the cell surface during live T-cell to B-cell cell-(immune cells) interactions and verifying a software model of diffusion of chemicals introduced into cells.

The following technical problem has remained unresolved by prior application software for automating an optical microscope system: namely, how to acquire images using a camera in an optical microscope system, operating at close to its maximum rate of acquisition, at the same time that external devices to the camera are continuously changing the settings of various parameters of image acquisition. The present invention solves this technical problem by providing a computerized method whereby the camera and the external devices in an automated optical microscope system are instructed to operate asychronously, that is, independently of each other, during image acquisition, thereby enabling the camera to acquire images that may be displayed as a sequence showing continuous change in image acquisition parameters.

SUMMARY OF THE INVENTION

The present invention provides a method, a computer readable medium and an automated optical microscope system for acquiring images at substantially the maximum acquisition rate of a camera while and as devices external to the camera change acquisition parameters. The stack of images so acquired images may be displayed as a sequence of images showing continuous change in the image acquisition parameters. Because the present invention directs external devices to change image acquisition parameters while and as a camera is acquiring each frame in a set of frame images, instead of directing the devices to wait until the camera has finished acquiring that frame, the camera and the external devices operate asynchronously. In different terms, the present invention directs external devices to operate to change the image acquisition parameter they control, for example, the focus position of the microscope objective lens, the emission and/or excitation wavelength or the position of the microscope stage, while and as a camera is acquiring an image.

The method of the present invention comprises the following steps:

a) configuring an image-acquiring system comprising an automated microscope, a camera, devices external to the camera for altering the image acquisition parameters of focus plane, excitation wavelength and/or emission wavelength and a computer, whereby the external devices are directed to acquire images asychronously with the camera;

b) acquiring images at a rate substantially close to the maximum image acquisition rate of the camera and storing the acquired images as digitized data;

c) during the acquiring and storing of images, operating at least one said external device whereby at least one image acquisition parameter is altered;

The method of the present invention may be used under a wide variety of microscopy modes, including brightfield, fluorescence, darkfield, phase contrast, interference, and differential interference contrast (DIC). One of the embodiments of the method of the present invention is as a set of instructions resident in an information handling system. Another embodiment of the method of the present invention is as a set of instructions resident in a computer readable medium.

It is a feature of the present invention that a group of images, called a stack, may be acquired as the focus position changes are made so that the group of images so acquired may be displayed as a sequence showing continuous change of the Z-position. It is a further feature of the present invention that a stack of images may be acquired as changes to the emission and/or excitation wavelength are made so that a group of images may be displayed as a sequence showing continuous change of the emission and/or excitation wavelength. Further, it is a feature of the present invention that a stack of images may be acquired as changes to various acquisition parameters, such as the focus position and the emission and/or excitation wavelength are made in concert so that a group of images displayed as a sequence show continuous change in the various acquisition parameters selected. A feature of another embodiment of the present invention is that at regular time intervals, a stack of images may be acquired while and as various image parameters are simultaneously changed so that the stacks of images may be displayed as a sequence that shows continuous change over time and continuous change in acquisition parameters.

An advantage of the present invention is that a stack of images allows a three-dimensional rendering of the relevant cellular mechanism, process, and/or structure during a biological event, such as the introduction of a chemical into a cell or cell division. A further advantage is that multiple stacks of images allow a three-dimensional rendering of a biological event of interest as image acquisition parameters change and over a selected time period.

BRIEF DESCRIPTION OF THE DRAWINGS

FIG. 5 is a flow chart diagram depicting an exemplary embodiment of the overall method of the present invention.

FIG. 7D shows the Camera Parameters user interface dialog of the Stream Acquisition embodiment of the present invention.

DETAILED DESCRIPTION

Figure 1:
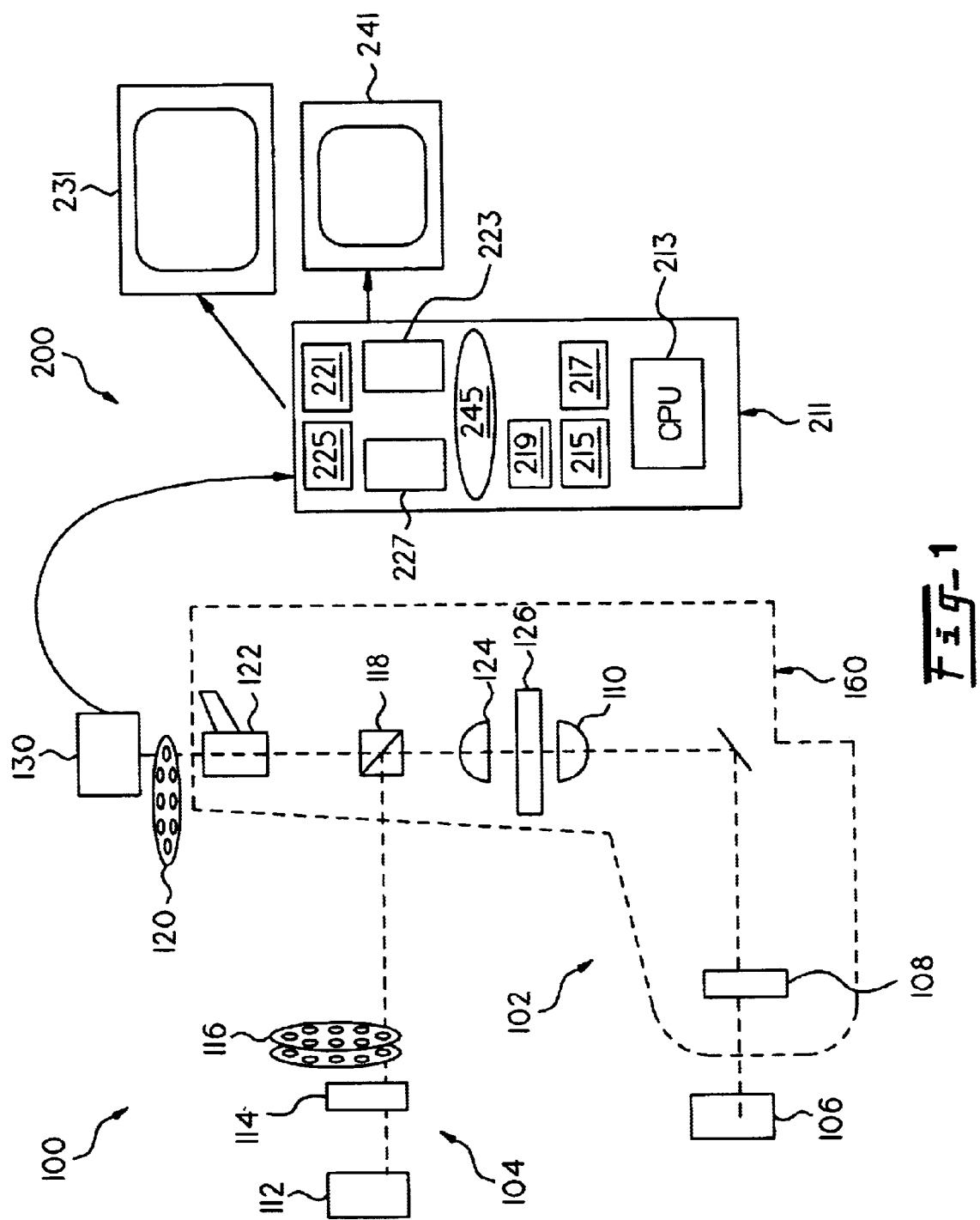
FIG. 1 is a block diagram of an automated optical microscope system that provides the operating environment for an exemplary embodiment of the present invention.

The present invention provides a method, a computer readable article of manufacture and an automated optical microscope system for acquiring images at substantially the maximum acquisition rate of a camera while and as external devices to the camera continuously change image acquisition parameters thereby allowing such images to be displayed as a sequence showing continuous variation in those parameters.

Definitions

Stack. As used herein, stack refers to the total set of images acquired by a method of the present invention during one acquisition event that may admit of image processing.

Focus Plane. As used herein, a focus plane is that vertical position at which the object of interest is being observed and brought into visual focus.

Z-position. As used herein, Z-position refers to the focus plane, which is that vertical position at which the object of interest is being observed and brought into visual focus. Z-position is an image acquisition parameter that may be varied by moving the objective lens positioner or by moving the stage mover of an optical microscope.

Image Acquisition Parameter. As used herein, image acquisition parameter includes the Z-position and the illumination wavelengths, which include either or both the excitation wavelength and the emission wavelength.

Piezofocuser. As used herein, a piezofocuser is a shorthand term for a piezoelectric objective lens positioner that operates to change the focus position in speeds that range from 1 to 2 milliseconds.

Asynchronous operation. As used herein, asynchronous operation means the simultaneous operation of a camera in acquiring images while and as external devices, such as an objective lens positioner, a stage mover and/or a wavelength changer, vary the specific image acquisition parameter each controls.

Inter-Frame Time. As used herein, inter-frame time is the time between the end of exposing one frame and the start of exposing the next frame. For a raster-scanned video camera, this is the time between the raster scan of the last digitized scan line of one frame and the raster scan of the first digitized scan line of the next frame. For a full-frame CCD camera, this is the read out time of the full frame. For a frame-transfer CCD camera, this is the frame transfer shift time.

General Organization of the System

FIGS. 1 to 4 and the following discussion are intended to describe an exemplary optical microscope system of the present invention. The system of the present invention comprises an automated optical microscope system comprising an information handling subsystem for executing a method of the present invention. The method comprises acquiring images at substantially the maximum acquisition rate of a camera while and as external devices to the system microscope are changing image acquisition parameters.

Those skilled in the art will appreciate that the invention may be practiced with a variety of information handling configurations, including a personal computer system, microprocessors, hand-held devices, multiprocessor systems, minicomputers, mainframe computers, and the like. In addition, those skilled in the art will appreciate that the invention may be practiced in distributed computing environments where tasks are performed by local or remote processing devices that are linked through a communications network or by linking to a server connected to the Internet through which the software method may be accessed and used.

Moreover, those skilled in the art will appreciate that specific research goals and needs will dictate the configuration and specific apparatus used in an automated optical microscope system, especially as these goals relate to processing images of living cells during biological events. The elements of an image processing system that utilizes the program module of the present invention comprise a microscope, a camera, means for processing the images according to the instructions of the program module of the present invention, and at least one means external to the microscope for varying at least one image acquisition parameter.

FIG. 1 shows a block diagram of an exemplary system of the present invention, having an optical microscope subsystem 100 and an information-handling subsystem 200. In this diagram, the microscope subsystem 100 has been depicted as to its most generic parts and should not be construed as limiting.

The exemplary microscope subsystem 100 comprises an optical microscope 160, shown here for illustrative purposes as an upright microscope. Devices external to the microscope 160 include an epi-illumination assembly 104, an emission wavelength changer 120 and a camera 130. The microscope 160 comprises a transmitted light illumination arm 102, which comprises elements 106 through 110, including a transmitted light source 106—typically a halogen lamp, a transmitted light shutter 108, and a condenser 110. The microscope 160 also comprises an ocular 122, a stage 126 and an objective lens 124.

The epi-illumination assembly 104 comprises elements 112 through 116, including an epi-illumination light source 112, which for illustrative purposes comprises a fluorescence lamp 112, a shutter 114, and an excitation wavelength changer 116. Camera 130 is connected to both the microscope subsystem 100 and the information handling system 200.

Figure 3:
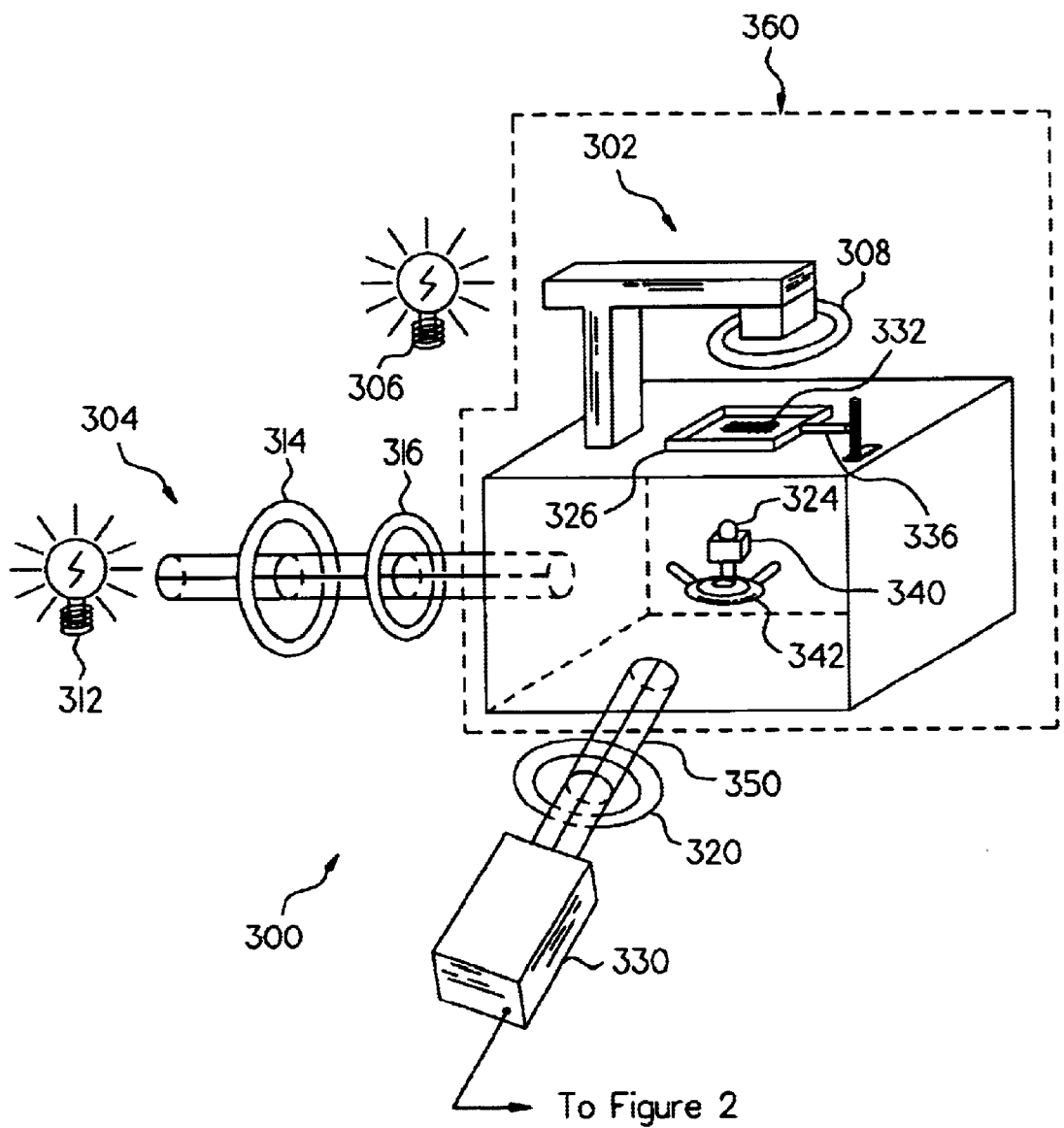
FIG. 3 shows a schematic diagram of an exemplary microscope subsystem used to practice a method of the present invention.

The information handling subsystem 200 as shown in FIG. 1 comprises an exemplary computer 211, illustrated here as a personal computer 211, comprising a central processing unit 213, a hard drive 215, a CD-ROM 217, a floppy drive 219, a graphics adapter 221, an ethernet network card 223, a PCI card 225 to interface computer 211 to camera 130 and a Digital to Analog converter [DAC] card 227 to control a piezoelectric objective lens positioner (340 in FIG. 3) and, if included in microscope subsystem 100, a monochromator fluorescence illuminator (not shown) that serves the same purpose as an excitation wavelength changer (116 in FIG. 1, 316 in FIG. 3). Peripherals in information handling system 200 comprise a graphics display monitor 231 and a video monitor 241. Application software 245 allows control of the components of microscope subsystem 100, specifically controlling the illumination, focus and the camera as well as directing the image acquisition and processing. The method of the present invention may be operated as a program module of application software 245.

Figure 2:
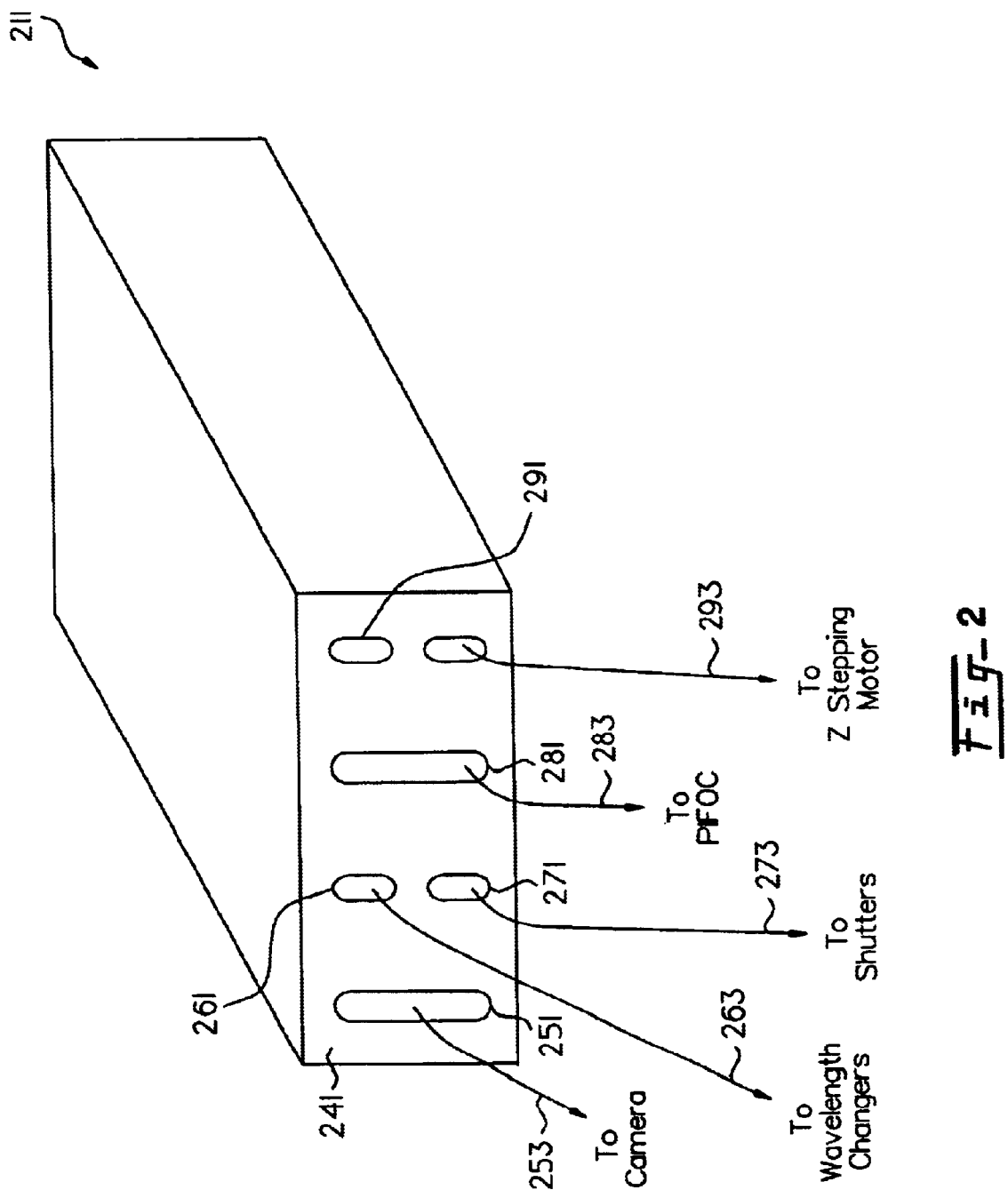
FIG. 2 shows a graphical representation of an exemplary hardware connection arrangement between an exemplary embodiment of an information handling subsystem and a microscope subsystem.

FIG. 2 shows a graphical representation of an exemplary hardware connection arrangement between an exemplary embodiment of information handling subsystem 200 and optical microscope subsystem 100. FIG. 2 shows an embodiment of a computer in the form of a personal computer 211. The back side 251 of computer 211 shows various serial and parallel ports, 251, 261, 271, 281 and 291, and physical connections 253, 263, 273, 283, and 293 by which computer 211 communicates with and controls various external devices of optical microscope subsystem 100. The ports and connections shown include a port 251 from which a connection 253 attaches to a camera (130 in FIG. 1, 330 in FIG. 3); a port 261 from which a connection 263 attaches to the emission and/or excitation wavelengths changers (116 and 120 in FIG. 1, 316 and 320 in FIG. 3); a port 271 from which a connection 273 attaches to external shutters (114 in FIG. 1, 314 in FIG. 3); a port 281 from which a connection 283 attaches to a piezoelectric objective positioner (340 in FIG. 3); and port 291 from which a connection 293 attaches to a stage mover (336 in FIG. 3).

FIG. 3 shows a schematic diagram of another embodiment of an optical microscope subsystem 300, used to practice the method of the present invention. Although the details of FIG. 3 parallel those of the block diagram of microscope subsystem 100 shown in FIG. 1, FIG. 3 provides a more graphical representation of the relationship between a microscope and a camera used in a system of the present invention.

The microscope subsystem 300 in FIG. 3 comprises a microscope 360, which for illustrative purposes is depicted as an inverted microscope, as well as devices external to the microscope 360 which include an epi-illumination assembly 304, an emission wavelength changer 320 and a camera 330. Microscope 360 comprises a transmitted light illumination arm 302, which comprises, a light source 306, exemplified as a halogen lamp 306, and a shutter 308. The epi-illumination assembly 304 comprises an epi-illumination light source 312, here exemplified as a fluorescence lamp 312, an epi-illumination shutter 314, and an excitation wavelength changer 316.

A specimen 332 to be observed is placed on microscope stage 326, which may be moved vertically up or down by stage mover 336, depicted in FIG. 3 as a mechanized stepper motor 336. A piezoelectric objective lens positioner 340 encases objective lens 324 and moves lens 324 vertically up or down in order to bring the specimen 332 in or out of visual focus. A revolving nosepiece 342 may be equipped with more than one objective lens 324.

Camera 330 is connected to microscope subsystem 300 via camera port 350. An emission wavelength changer 320 is placed between microscope 360 and camera 330.

Figure 4:
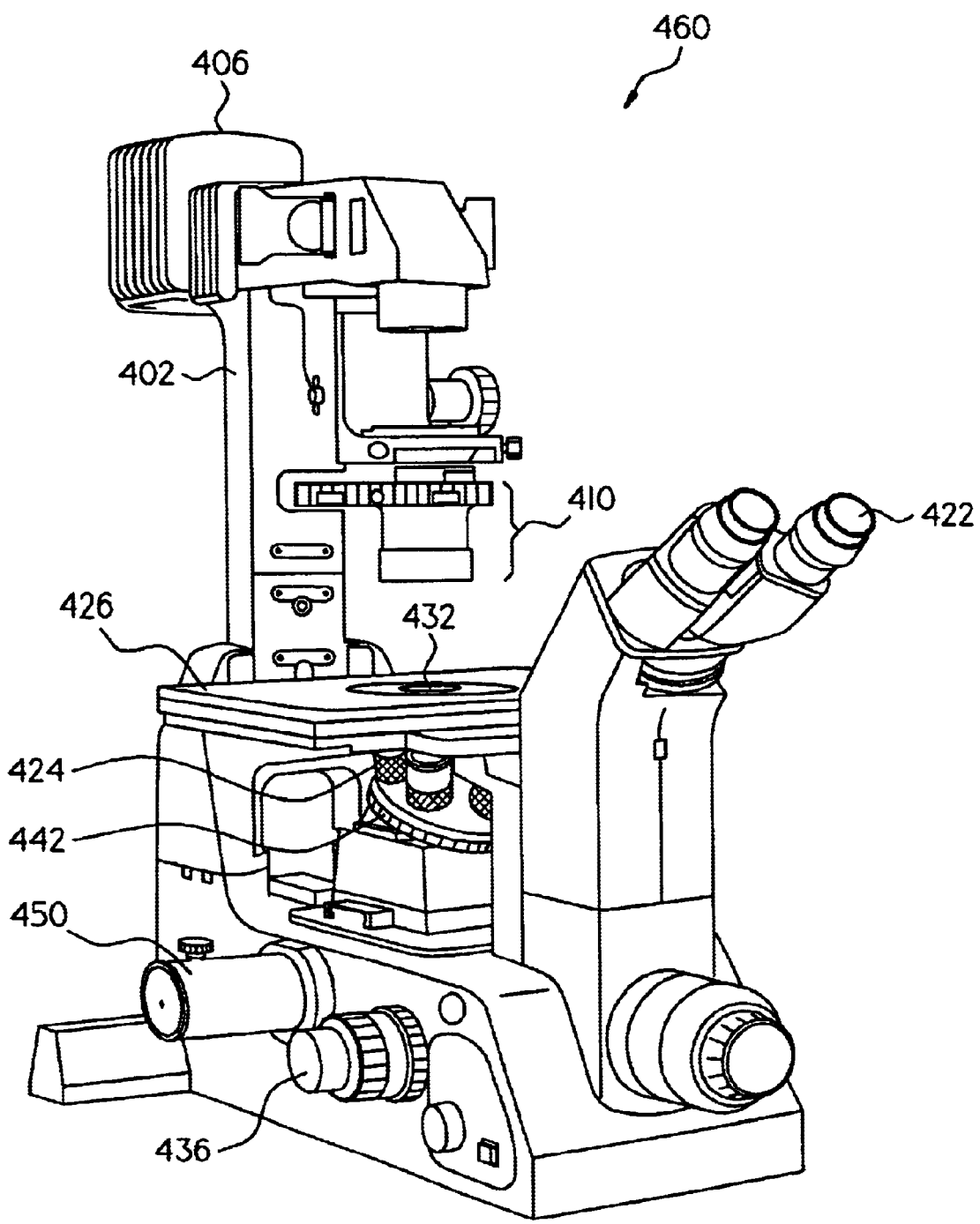
FIG. 4 shows a graphical representation of an exemplary microscope used to practice a method of the present invention.

FIG. 4 shows a graphical representation of an embodiment of a microscope 460 used in a system of the present invention. The transmitted light illumination arm 402 houses a transmitted light 406 and comprises a condenser 410. A researcher may manually bring a specimen 432 placed on stage 426 into focus by looking through the ocular 422 and operating a stage mover 436, depicted in FIG. 4 as coarse/fine focusing knob 436. If desired, a stepper motor (not shown) may be attached to the focusing knob 436 to mechanize stage movement.

An epi-illumination assembly (not shown) that would comprise an epi-illumination light source, a shutter and an excitation wavelength changer (all not shown) could be attached to microscope 460 behind the revolving nosepiece 442 and objective lens 424. A piezoelectric objective lens positioner (not shown) may be fitted over objective lens 424. An emission wavelength changer (not shown) may be connected to the camera port 450, which connects the microscope 460 to a camera (not shown).

How the Automated Microscope System Works

With continuing reference to FIG. 3, the automated microscope system 300 is directed by a method of the present invention to acquire images as viewed through an optical microscope 360 and to store those images as digitized data at or near the maximum acquisition rate of the acquiring camera 330. At the same time, the method is also directing external devices 340, 336, 316 and 320 to change a parameter related to image acquisition, that is, the focus plane of the specimen and/or excitation and/or emission wavelengths. A focus plane is that vertical position at which the object of interest is being observed and brought into visual focus. A focus plane may be altered by changing the vertical position of either objective lens 324 (by using objective lens positioner 340) or stage 326 (by using stage mover 336). As used herein, the term Z-position will refer to the focus plane, which may be changed by either an objective lens positioner 340 or a stage mover 336.

Thus, system 300 of the present invention functions to acquire images by having a programmed set of instructions to perform the method of the present invention by directing camera 300 and external devices 340, 336, 316 and 320 to operate asynchronously during image acquisition which is done at or near the maximum rate of camera 300. As pointed out above, external devices 340, 336, 316 and 320 include objective lens positioner 340 that moves objective lens 324 vertically up or down, a stage mover 336 that moves microscope stage 326 vertically up or down and wavelength changers 316 and 320, which change the wavelength of light used to excite the specimen and/or filters the light emitted from specimen 332.

To appreciate how the present invention works, it is important to remember that observations of living cellular material must occur at rates that correspond to the rates at which the observed processes are occurring. Typically, camera 330 must acquire images of biological events at the cellular level in the real time of milliseconds.

The interaction between a camera, an automated microscope and external devices

In observing events in living cells and tissues, microscope subsystem 300 is set up, that is, configured, so that camera 330 acquires images as essentially 2-D "snapshots" at different depths of the three-dimensional living structure at issue. Changing the vertical position of objective lens 324 in effect changes the depth of the focus at which the 2-D "snapshot" is taken within the cell. Changing the focus depth literally changes the perceptibility of different cellular structures and processes that lie at different depths within the cell. Every time objective lens 324 changes position, a different focus is achieved, which brings a different visual perspective of internal cell structure. Rapidly acquiring "snapshots" from a camera as the vertical position of the focus changes results in a set of "photographs" that can be displayed as a sequence or movie of images, which can on playback allow a researcher, for example, to look from top to bottom (or vice versa) through a cell. A set of images acquired by system 300 for a particular number of vertical positions (and/or selected wavelengths as discussed below) is a stack.

For example, if a researcher wishes to observe an event occurring at or on the membrane of the outer cell wall, typically a researcher will first eye-focus microscope 300 by manually directly a mechanism 336 to move stage 326 to a vertical position so that the outer cell membrane comes into visual focus. Then, while camera 330 acquires images of the cell membrane, a researcher can opt to vary the focus position by moving objective lens 324. In a system of the present invention, a software method of the present invention will direct a mechanized device called a piezoelectric objective positioner 340, hereinafter called a piezofocuser, to vertically move objective lens 324 to focus on different depths within the cell membrane. Each position to which objective lens 324 moves is termed in the art a Z-position. Since distances between Z-positions for cellular research are in terms of nanometers, using a piezoelectric mechanism to move the objective lens allows the precise motion and positioning necessary without machine slippage and occurs typically at a rate of 2 milliseconds (ms). This is most often sufficiently rapid to allow camera 330 to acquire a stack of images at different focal depths so that the stack displays on playback a rapidly occurring biological event at the cell membrane.

In addition to varying the Z-positions of objective lens 324, subsystem 300 may also be configured to vary the wavelengths of light used to illuminate specimen 332 during the acquisition of a stack of images. Cellular structures, processes and events of living cellular material are often observed using fluorescence microscopy by introducing fluorescent chemical or protein probes. Further, the ability to solve problems using fluorescence microscopy is enhanced by the systematic varying of the wavelength of light used to excite a fluorescently stained specimen or the filtering of the light that is emitted from the specimen.

Different fluorophores, fluorescent chemical or protein molecules, absorb and become excited by electromagnetic radiation at specific wavelengths of light and emit fluorescence at specific wavelengths of light. Moreover, cellular structures stained with different fluorescent dyes are excited by and emit fluorescence with different wavelength ranges of light. By restricting or filtering the wavelength of excitation light shone on a fluorescently stained specimen or the wavelength of emission light captured by camera 330, a researcher can observe different cellular structures or cellular events both through time and at different depths within a cell or tissue. In addition, by so restricting or filtering the fluorescence excitation and/or emission wavelengths, a researcher can highlight selected cell structures or measure conditions within cellular structures.

For example, by staining a cellular organelle situated near the outside cell membrane with fluorescent dye A and staining the chromosomes situated in the cell nucleus with fluorescent dye B, a researcher can acquire a stack of images that focus on different cellular events involving both organelles. This is so because of the nature of fluorescent dyes. Say, for example, that fluorescent dye A is excited at wavelength A and fluorescent dye B excited at wavelength B. By switching back and forth between excitation wavelength A and B while camera 330 is taking 2-D "snapshots", a researcher can create a stack of images which on playback can be processed to display structures that are excited at only wavelength B or only wavelength A or at both wavelengths and so can tease out from a composite cellular event the changes within only one element of interest. This concept is analogous to a TV-watcher using a remote control to rapidly switch back and forth between channels as a camera is taking pictures of the TV screen after each channel switch.

In changing the excitation or emission wavelength, some wavelength changers can operate at a rate of 1.2 ms. For most cameras, this is sufficiently rapid to let camera 330 acquire a stack of images at different wavelengths so that the stack displays on playback a rapidly occurring biological event involving more than one cellular element or a biological process.

A system of the present invention may be set up to vary both the Z-position and the wavelength while camera 330 is acquiring images. When a researcher opts to change both the Z-position and the wavelength, the method of the present invention will first direct piezofocuser 340 to move objective lens 324 to a new Z-position, and then direct wavelength changer 316 and/or 320 to switch to a new wavelength. Only after camera 330 has finished acquiring images at each of the selected wavelengths will the method then direct piezofocuser 340 to move to a new Z-position. In theory, the method allows a researcher to select any number of wavelengths to switch between. An embodiment of the present invention allows a researcher to select four different wavelengths.

As mentioned above, piezofocuser 340 has the capability to change the Z-position of objective lens 324 in 2 ms and because wavelength changer 316 and/or 320 has the capability to change a wavelength in 1.2 ms, the system-limiting component in the subsystem 300 is most often camera 330. Ultimately, the rate at which camera 330 acquires images determines whether there is sufficient time for external devices 340, 336, 316 or 320 to change their respective parameters before the next image is acquired.

Operating Principles of the Method/System

At its essence, then, the method of the present invention relies on the difference between the acquisition rate of camera 330 and the operation rate of piezofocuser 340, stage mover 336, wavelength changers 316 and/or 320 in order to acquire a stack of images that can display on playback continuous change in the selected parameters. A fundamental operating principle of the present invention is that when camera 330 acquires images more slowly or almost as quickly as the external devices operate, then piezofocuser 340 and wavelength changers 316 and/or 320 can change the Z-position and wavelength respectively before the camera starts acquiring the next image. Put differently, camera 330 only has to be marginally slower than the external devices 340, 336, 316 and/or 320 in order for the Z-position and the wavelength to be varied quickly enough so that the next acquired image will capture and be able to display these changed values.

A second fundamental operating principle of a method of the present invention is that image acquisition occurs while and as piezofocuser 340, stage mover 336, wavelength changers 316 and/or 320 are operating asynchronously with camera 330. Asynchronous operation means piezofocuser 340, stage mover 336, wavelength changers 316 and/or 320 do not wait for a signal that the read out of the exposed image has finished before changing the Z-position and/or wavelength. Asynchronous operation means that during camera readout, the external devices are are either switching to the next desired wavelength and/or moving the focus plane to the next desired Z-position. In other words, camera 330 and external devices 340, 336, 316 and 320 are operating more or less simultaneously, and not sequentially. To the contrary, in a sequential, that is, synchronous, operation external devices 340, 336, 316 and/or 320 would in fact wait for camera 330 to complete acquisition and read out before receiving a signal to change parameters. Synchronous operation would therefore slow down the overall acquisition rate of the subsystem 300, thereby disallowing it to acquire images at or near real the maximum acquisition rate of camera 330, which is a primary object of the present invention.

Background to Cameras and Image Acquisition Rates

To provide a context and background for these essential operating principles of the present invention, the following paragraphs briefly discuss image acquisition by a camera. Image acquisition by a camera is fully and well-documented in Inoué and Spring, Video Microscopy, 2d. Edition, 1997, incorporated herein by reference, especially Chapter 5. Suffice it to say here that a camera converts an optical image exposed on its photosensitive surface into a sequence of electrical signals that make up the video signal. For cameras using the North American (NTSC) format, the optical image is sampled, that is, read out-from top to bottom and from left to right—as if it were a rectangular page that contains 525 horizontal scan lines every 1/30 of a second. This is termed a raster scan read out sequence. For cameras using the European (PAL) format, the read out rate is 525 horizontal scan lines every 1/25 of a second. These figures translate into the following standards: 1 frame is read out every 33 milliseconds for NTSC-format cameras, and 1 frame is read out every 40 milliseconds for PAL-format cameras. These standard read out rates hold true for a wide variety of video-rate cameras, whether vidicon tube cameras or solid state cameras. The latter camera uses photodiodes for photodetection. For a raster-scanned video camera, the inter-frame time is the time between the raster scan of the last digitized scan line of one frame and the raster scan of the first digitized scan line of the next frame.

One kind of solid state photodiode camera is a charge-coupled device (CCD) camera. The charge-coupled device of such cameras comprises a large rectangular array of photodiodes deposited on a silicon substrate. Each photodiode is a sensor element separated and isolated electrically from its neighbors by a channel stop. During the period of exposure, photons fall on the photodiodes while electrons in the depletion layer of each photodiode move into an adjoining isolated potential well. Each well collects a number of electrons, and hence stores a specific charge. Once all the wells in the rectangular array are detected by the camera as being filled—thereby signalling the end of exposure—read out of the stored charge occurs.

Read out for a CCD solid-state camera is done by shifting the electrons across the wells in a systematic fashion to an output node, where the electron charge in each well is "read" in the same raster scan sequence that the array of wells constituted in the photodiode array. The output node thus reads each well as having its own specific charge in a top-down, left-right sequence. The output node is connected to an amplifier that converts the charge in each well to a voltage, which is proportional to the stored charge in each well or pixel.

There are three most common arrangements of photodiode architecture in a charge-coupled device: full frame, frame transfer and interline. Full frame CCD architecture means that the entire photodiode frame is integrated, that is, exposed, to contain charge in all the frame wells before read out occurs. Consequently, for a full frame CCD camera, the inter-frame time is the read out time of the chip.

Full frame architecture is currently used in slow-scan CCD cameras that employ a mechanical shutter. The shutter is opened during image acquisition and closed during charge transfer and readout. The implication of full frame architecture is that the image acquisition rate is limited by the detector size of the photodiode array, the speed of the mechanical shutter and the read out rate of the image data from the charge-coupled device to the computer.

A camera using frame transfer CCD architecture divides the full frame of photodiodes into two regions: an imaging section and a masked, storage section. During integration (exposure), the image is stored as electron charge only in wells of the imaging section. Once exposure has completed, the stored charge is then shifted to the wells in the masked section very rapidly. After the stored charge has shifted to the masked section, two processes co-occur: the imaging section has been freed up to start exposure again while the masked section reads out the stored charge from the first exposure. Consequently, the inter-frame time of this kind of CCD camera is the time it takes the stored charge to shift from the imaging section to the masked section. Frame transfer CCD cameras can perform the dual tasks of exposing and reading out almost simultaneously.

In a camera with interline CCD architecture, the full frame of photodiodes are arranged in alternating columns so that one column contains imaging photodiodes and the next column contains masked ones. During integration, a column of imaging photodiodes transfers the charge in its wells to the neighboring column containing masked photodiodes section. As in the operation of a frame transfer camera, after the charge has been transferred to the masked columns, the unmasked columns of photodiodes can begin exposure again. Also similar to a frame transfer camera, Interline transfer cameras that contain overlapping masked and unmasked diodes perform image acquisition similarly as a frame transfer camera. For an interline CCD camera operating in sequential mode, the inter-frame time will be the same as for a frame transfer CCD, that is, the read out time of the photodiode array. If the interline CCD camera is operating in overlapped mode, the inter-frame time will be the shift time for transferring the charge stored under the masked section.

Configuration of the System and Asynchronous Operation of the External Devices

When external devices 340, 336, 316 and/or 320 operate at a rate either faster than or similar to the acquisition rate of camera 330, external devices 340, 336, 316 and/or 320 can operate asynchronously with camera 330, which in turn has implications for the organization of the system. When external devices 340, 336, 316 and/or 320 configured into the system allow asynchronous operation with camera 330, there is no need for direct connections between camera 330 and the external devices. Therefore, in a system of the present invention, external devices 340, 336, 316 and/or 320 are connected, for example, via connections 283 and 261 to the system computer 211. These devices are not connected directly to camera 330. Asynchronous operation occurs by having a software method of the present invention signal devices 340, 336, 316 and 320 to change parameter values in concert with the acquisition routine of camera 330.

Exposition of a Method of the Present Invention

At its most fundamental, the method of the present invention operates in the following way: The researcher configures the system to include camera 330 and the selected external devices 340, 336, 316 and/or 320. The researcher inputs the number of Z-positions and/or wavelengths at which images will be acquired. By so inputting, a researcher is in effect selecting the number of frames that camera 330 will acquire in any one stack during an experiment or acquisition event. For example, inputting 20 Z-positions and 2 wavelengths translates into a stack of 40 frames. The stack can be processed by appropriate application software, such as MetaMorph available from Universal Imaging, as a sequence that displays continuous change in the selected parameters of Z-position and wavelength.

Upon the researcher's command to begin image acquisition, the method directs camera 330 to begin exposing at the first selected Z-position and first selected wavelength. The image is digitized, a process well known in the art, then read out to computer 211 and stored as a digitized image in a temporary memory location or buffer. When camera 330 begins reading out the exposed image, the method directs external devices 340, 336, 316 and/or 320 to change values. Recall that if piezofocuser 340 and wavelength changers 316 and/or 320 are configured into the system, the method will direct wavelength changer 316 or 320 to switch to all selected wavelengths at the current Z-position before directing piezofocuser 340 to move objective lens 324 to the next Z-position. The method continues to direct external devices 340, 336, 316 and/or 320 to change values at the beginning of the read out for each image until these devices have moved through the entire set of selected values.

Critical to understanding the method of the present invention is that camera 330 is given free rein, so to speak, to acquire images at or near its acquisition rate while the method is directing the operation of external devices 340, 336, 316 and/or 320 to coincide with the read out from camera 330. Critical to one embodiment of a method and system of the present invention is the limitation that the operation rate of external devices 340, 336, 316 and/or 320 be the same as or faster than the inter-frame time of camera 330. For example, a researcher may employ a camera with a fast inter-frame time, that is, a frame transfer camera or an interline transfer camera operating in overlapping mode, which rivals the operation rate of piezofocuser 340 and/or wavelength changer 316 and/or 320 at about 1 to 2 milliseconds. In this embodiment, camera 330 will actually be acquiring images at the same rate as these devices 340, 336, 316 and 320 are changing Z-position or wavelength.

When the operation rate of external devices 340, 336, 316 and/or 320 is slower than the inter-frame of camera 330, the method cannot direct external devices 340, 336, 316 and 320 to change Z-position and/or wavelength while and as camera 330 is reading out the current image to computer 211. For example, using a slow wavelength changer to switch between selected wavelengths will result in images that will contain comingled wavelengths. To reduce image corruption, in this embodiment a researcher uses a method that directs camera 330 to forego exposing images at every frame but to skip a selected number of frames, for example, 3, before exposing the image. In doing so, the method of this embodiment effectively gives external devices 340, 336, 316 and/or 320 extra time to change parameters and to catch up with the camera.

Specific Apparatus and Application Software

Specific apparatus that may be configured into a system of the present invention so as to operate asynchronously using a method of the present invention include the following: the lines of MicroMax and PentaMax cameras available from Roper Scientific, Princeton Instrument division as well as the line of Coolsnap FX cameras, available from the Photometrics division of Roper Scientific. Also, the system and method of the present invention may be operated with any camera complying with the RS-170 or CCIR standards so long as it is interfaced to the processor through a digitizer card called a video frame grabber. An example of a video frame grabber that can create a software interrupt so that the method of the present invention can direct a camera to acquire images simultaneously as the external devices are varying is the FlashBus MV PRO PCI bus-mastering digitizer card.

Piezofocusers that may operate within the system and method of the present invention include the PIFOC® line of Microscope Objective Nanopositioners available from Physik Instrumente. Suitable wavelength changers that may operate within the system and method of the present invention include the following: Lambda DG5 Illuminator, Lambda DG4 Illuminator, Lambda 10-2 Wavelength changer and Lambda 10 Wavelength Changer, all available from Sutter Instruments; Polychrome II Monochromator available from TILL; Monochromator available from Kinetic Imaging; and DeltaRAM Monochromator available from PTI.

Application software that would support asynchronous operation of a camera and external devices include MetaMorph™ and MetaFluor®.

Exemplary Information Handling SubSystem

With reference to FIG. 1, when information handling subsystem 200 comprises a computing device 211 in the form of a personal computer, an exemplary subsystem 200 of the present invention may employ a processor of the Intel Pentium III class, which currently includes 550 MHz, 700 MHz, 750 MHz, 800 MHz or 850 MHZ. Preferred motherboards include either the P3BF or CUBX av available from Asus. For display adapters, a researcher may the ATI Expert@Play 98—8 megabyte; the Matrox G400—32 megabyte dual display or the ATI Rage Fury Pro—23 megabyte.

Recommended memory requirements for the configured system are 256 megabytes to 1 gigabyte SDRAM memory. Regarding the various drives: recommended is a WDC WD205BA IDE (20.4 gigabyte) hard drive available from Western Digital; a 1.4 megabyte 3.5 floppy drive; and a CD-R58S read/write 8×24 SCSI CD-ROM drive.

Recommended cards include—for the SCSI card: the Adaptec 2930 Ultra SCSI2 kit; for the Input/Output card: the SIG Cyber PCI—1 serial, one parallel port; for the Network Card: the 3COM 3C905TX-M 10/100 PCI.

Method

With continuing reference to FIGS. 1 and 3, FIG. 5 shows a flow chart of a method of the present invention. Although a method of the present invention is described hereinbelow in terms of a computer program module for acquiring images at substantially the maximum acquisition rate of a camera while and as external devices to the camera continuously change image acquisition parameters, those skilled in the art will recognize that the invention may be implemented in combination with other program modules, routines, application programs, etc. that perform other, particular tasks.

The image acquisition parameters that may be varied while and as an image is acquired include the Z-position, the excitation and/or emission wavelengths, and the vertical position of the microscope stage. The Z-position may be changed either by moving relative to the sample objective lens 324 using a piezofocuser 340 or by moving microscope stage 326 using stage mover 336. The image acquisition parameters as shown in FIG. 5 include the Z-position and the wavelength.

Configuring the System

Before camera 330 begins acquiring images, the researcher will already have established the research goals and prepared specimen 332 and will be ready to configure, that is, identify to the system, the specific hardware the system will be using. As shown in FIG. 5, a method of the present invention commences at step 500 with the researcher configuring a system of the present invention by selecting specific image acquisition devices. Configuring the system is actually the selection of appropriate device drivers, which are software files pre-stored in an image acquisition/processing program that contain information needed by the program module to operate the corresponding hardware. Configurable image acquisition devices include camera 330, means for changing the Z-position, which include piezofocuser 340 and stage mover 336, and wavelength changers 316 and 320.

Figure 6A:
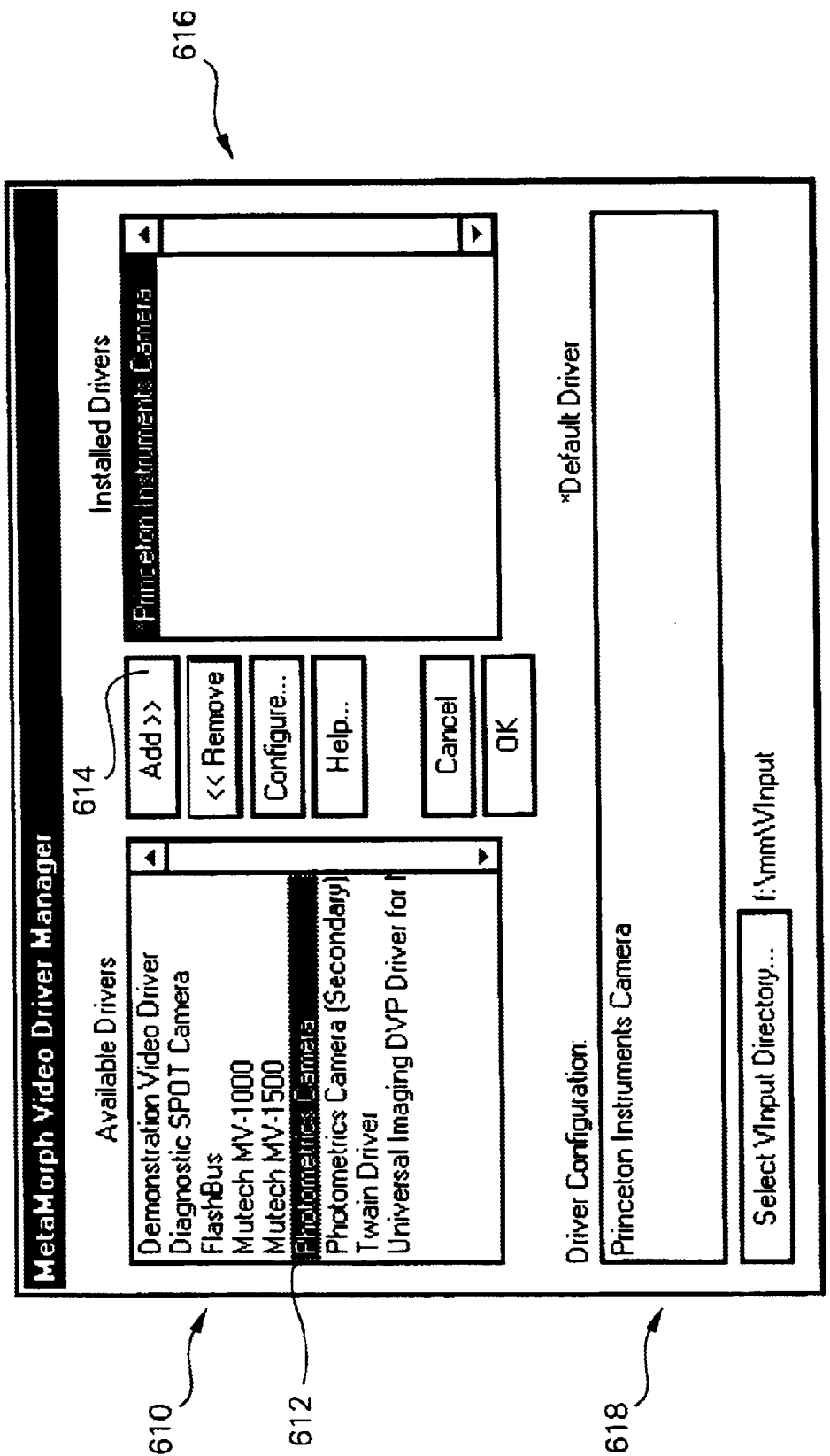
FIG. 6A shows an exemplary user interface dialog for installing a camera into a system of the present invention.

With continuing reference to FIGS. 3 & 5, FIGS. 6A–D show exemplary user dialogs for configuring an automated optical microscope subsystem 300. FIG. 6A shows an exemplary dialog for installing camera 330. Shown to the left is a list of available camera drivers 610 contained in an exemplary software package for image acquisition/processing 245. Highlighting a particular driver 612 from the Available Drivers 610 list and clicking the Add 614 button results in the selected driver appearing in the list of Installed Drivers 616. The system as exemplified in the Driver Configuration 618 window is configured to contain. only one camera.

Figure 6B:
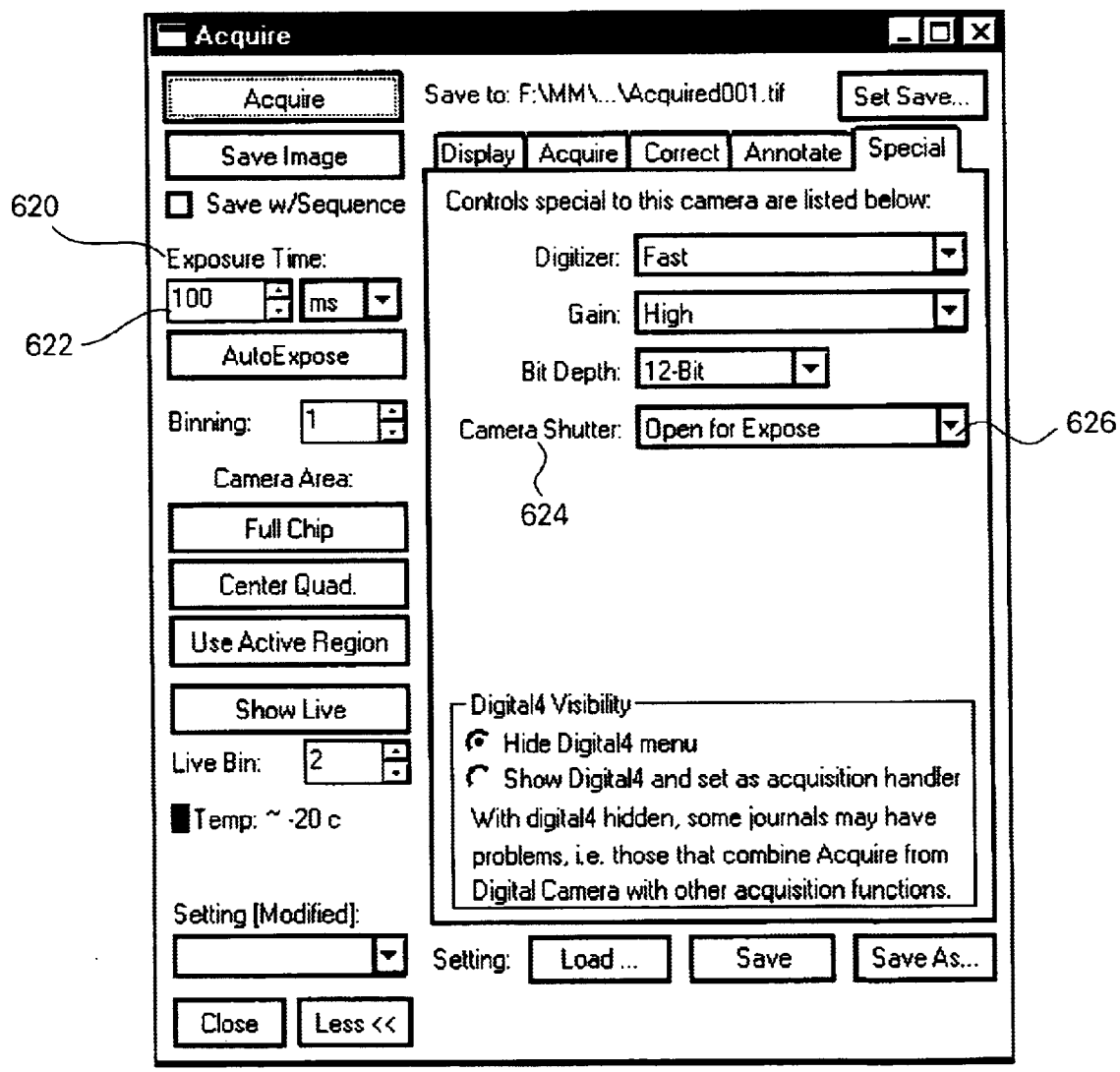
FIG. 6B shows an exemplary user interface dialog for configuring parameters relating to the installed camera in FIG. 6A.

FIG. 6B shows an exemplary dialog for configuring parameters relating to the installed camera in FIG. 6A, particularly Exposure Time 620 and Camera Shutter 622. Exposure Time 620 means the total exposure duration and is exemplified at 620 as 100 ms. The user may also select at 626 to have the camera shutter remain open during the exposure time. By so selecting and by configuring a wavelength changer (316, 320) into subsystem 300 as shown below in FIG. 6C, a researcher can operate wavelength changer (316, 320) as a shutter for system 300.

It is important to note that mechanical shutters external to camera 330 such as shown at 308 or 314 in FIG. 3 must run at a cycle time greater than 25 ms because they are driven by a high voltage that takes time to dissipate. Running these shutters at a cycle length shorter than 25 ms will cause a build-up of heat, leading to eventual jamming. For that reason, it is useful to allow a fast wavelength changer, with a 1.2 ms switch time, to operate as a shutter. This allows camera 330 to acquire images at or near its maximum acquisition rate and thereby to promote asynchronous operation with external devices 340, 336, 316 and/or 320.

Figure 6C:
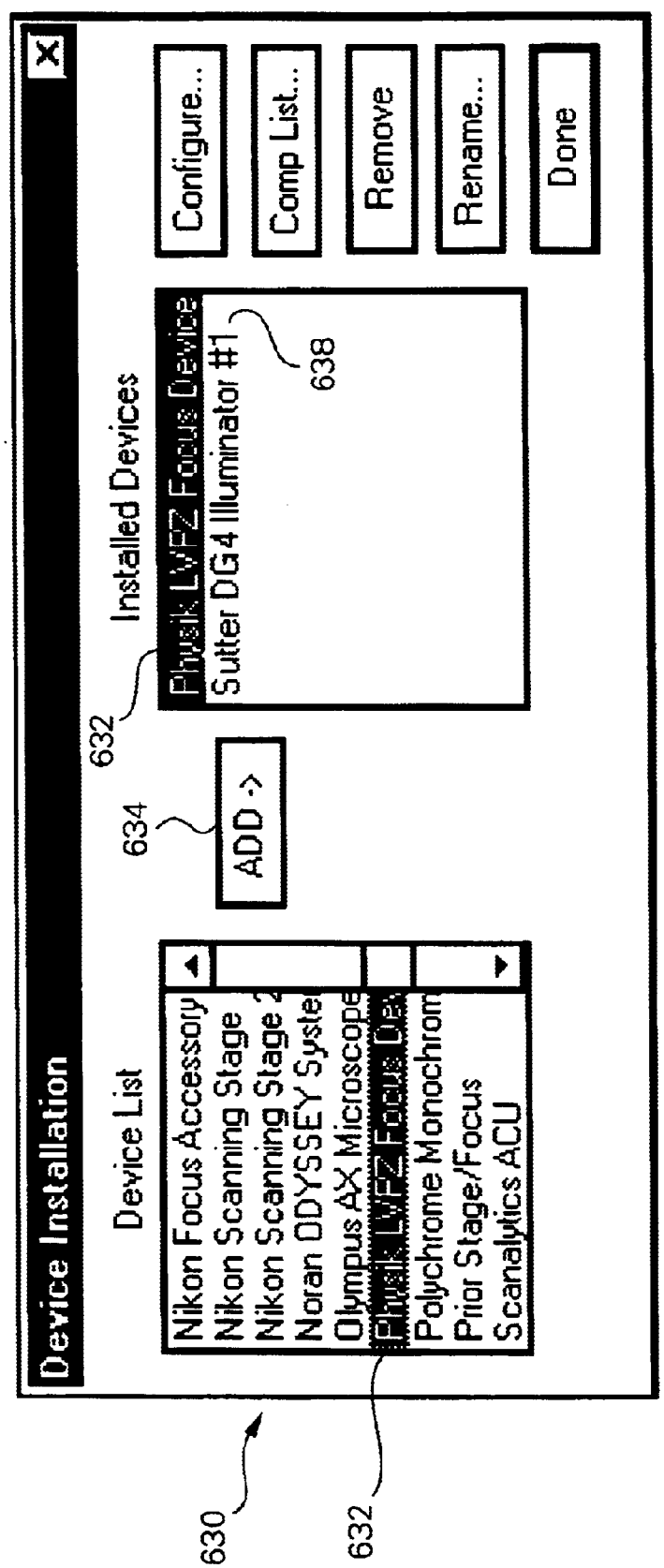
FIG. 6C shows an exemplary user interface dialog for installing into a system of the present invention a device external to the microscope that varies image acquisition parameters.

FIG. 6C shows an exemplary dialog for installing an external device into the system. Highlighting the name of a specific device at 632 and clicking the Add 634 button results in device 632 appearing in Installed Devices 636. As shown in FIG. 6B, two external devices have been installed in an exemplary system, a piezofocuser at 632 and a wavelength changer at 638.

Figure 6D:
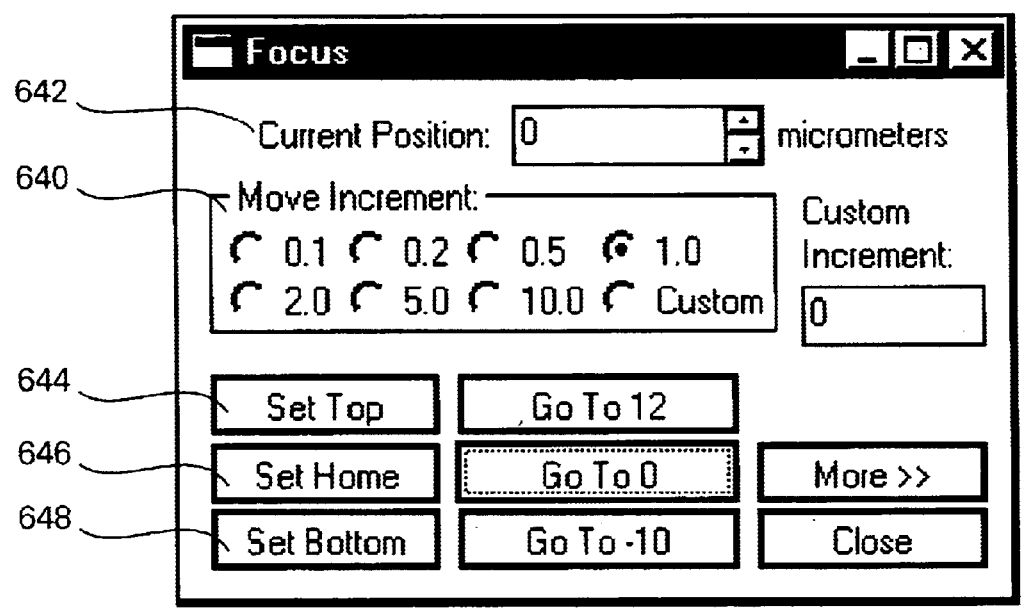
FIG. 6D shows an exemplary user interface dialog for configuring an installed objective lens positioner into a system of the present invention.

FIG. 6D shows an exemplary dialog for configuring a piezofocuser installed into system 300. On the bottom of the dialog are shown three buttons 644, 646 and 648 by which a researcher determines the range of the distance over which piezofocuser 340 may move objective lens 324. By clicking on Set Home 646, a user sets the Home position to which piezofocuser 340 moves objective lens 324 at the end of image acquisition. Home is an arbitrary position and depends on the research goals. For example, a researcher may have determined by eye-focus or from processing previously acquired stacks events a certain critical Z-position; such a Z-position would be set as Home. The Set Top 644 position is the maximum upper limit above Home to which objective lens 324 may move; the Set Bottom 648 position is the maximum lower limit below Home. Together the Top, Home and Bottom positions define the total distance over which piezofocuser 340 may move objective lens 324 during the exposure time. A researcher can initialize the starting position of objective lens 324 by keying in a Current Position 642. The Move Increment 640 option allows a user to select the incremental distance between Z-positions, which, as shown, is set at an exemplary 1.0 micrometers.

By setting the Top and Bottom positions at 644 and 648 as well as the Move Increment at 640, a researcher can calculate the total number of Z-positions at which images will be acquired. For example, in FIG. 6D, the total vertical distance over which a piezofocuser will move is 22 micrometers; at an incremental distance of 1 micrometers, images will be acquired at a minimum of 23 Z-positions (the start position=1 plus 22 micrometers=23 total positions).

User Input

Referring back to FIG. 5, the next step in the method after configuring the system is User Input at step 502. Here the user inputs a range of values so that the method can direct piezofocuser 340 and wavelength changers 316 and/or 320 to change to specific Z-positions and wavelengths during image acquisition.

Stream Acquisition Embodiment of User Input

FIGS. 7A–D show a first embodiment of user dialogs for inputting Z-position and wavelength values, illustrated as the Stream Acquisition 702 Embodiment. FIGS. 8A–H show a second embodiment of such user dialogs, illustrated as the Multi-Dimensional Acquisition 802 Embodiment.

Figure 7A:
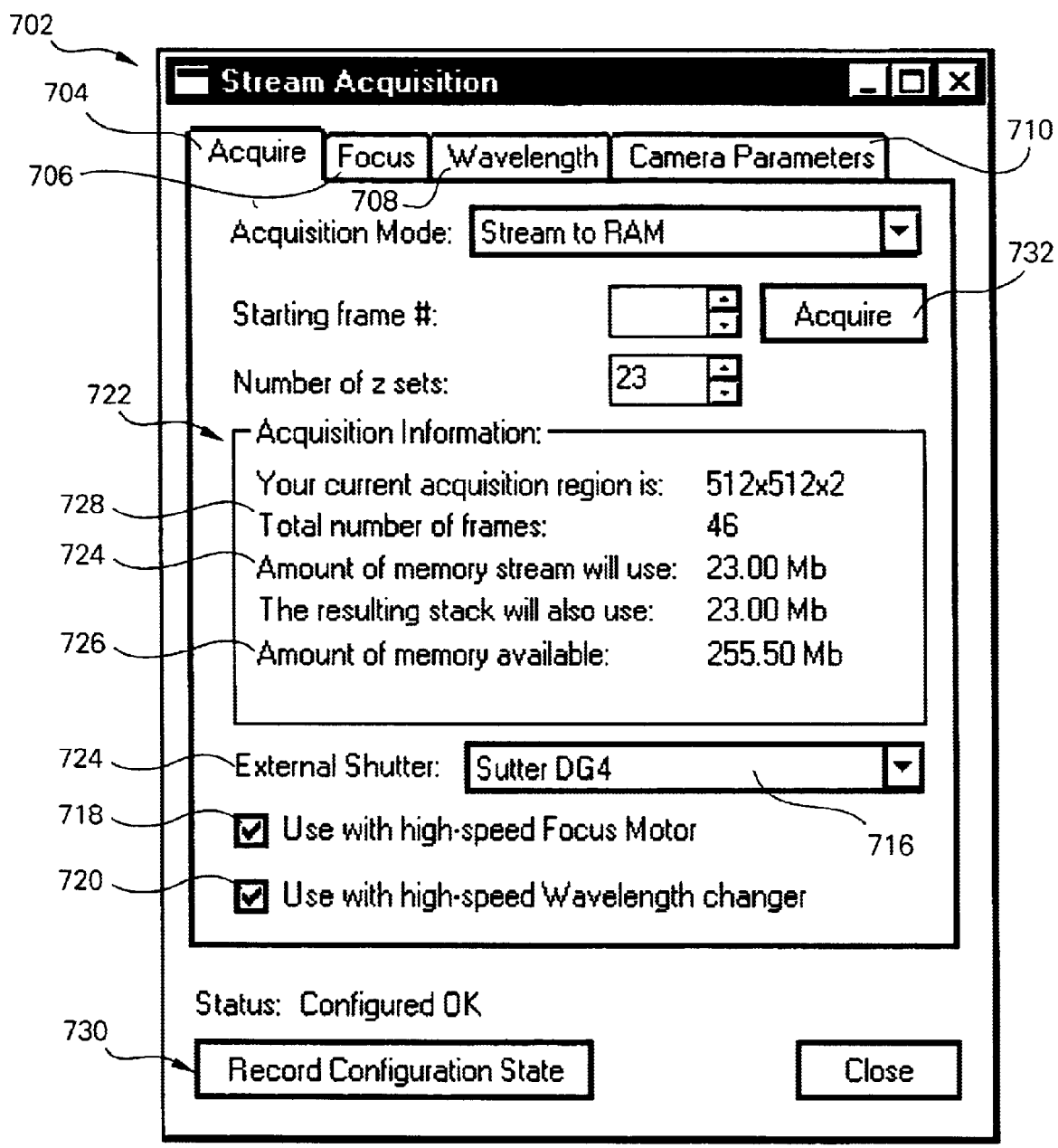
FIG. 7A shows the Acquire user interface dialog of the Stream Acquisition embodiment of a method of the present invention.

FIG. 7A shows that Stream Acquisition 702 embodiment contains four separate user dialogs or tabs—Acquire 704, Focus 706, Wavelength 708, and Camera Parameters 710—by which a researcher may input values for acquisition conditions. FIG. 7A shows the Acquire 704 dialog and illustrates a user's selections within that dialog. Options 718 and 720 allow a researcher to check that camera 330 will be operating with a piezofocuser and a highspeed wavelength changer. By checking 718 and 720 and by having already configured the specific devices into the system as shown in FIG. 6C, a user receives confirmation at field 730 that the installed devices support and are capable of asynchronous operation with the camera during image acquisition.

In both the Stream Acquisition 702 and the Multi-Dimensional Acquisition 802 embodiments, a user may choose to acquire images while and as both a piezofocuser 340 or stage mover 336 and wavelength changers 316 and/or 320 vary the Z-position and the excitation and/or emission wavelengths. This relates to the fundamental operating principles of the method discussed hereinabove. Because external devices 340, 336, 316 and 320 operate asynchronously with camera 330, the external devices do not wait for the camera to finish readout before changing their respective parameters. In one embodiment of the method, therefore, so long as each external device is operating faster or near the inter-frame time of the camera, several external devices may be configured together so that they are all operating to change their image acquisition parameters as the camera is acquiring. In practice, however, although the camera and external devices operate asynchronously, the external devices operate synchronously relative to each other. More specifically, when, as shown at fields 718 and 720 in FIG. 7A, a researcher selects to use both piezofocuser 340 and wavelength changer 316 and/or 320, the method signals the piezofocuser 340 first to move to a new Z-position. The system of the present invention then signals the wavelength changer 316 and/or 320 to change to each selected wavelength in successive frames. Only after a frame has been exposed at each of the selected wavelengths will the method signal to the piezofocuser 340. to change Z-position. The sequential operation of the external devices relative to each other is more fully illustrated in FIG. 10.

FIG. 7A also shows that a user may select the number of Z-positions to which piezofocuser 340 will move objective lens 324, illustrated at field 712 as 23. In theory, a user may select any number of Z-positions at which to acquire images and is constrained by the biological entity of interest and the research goals and not by the present method of operating a camera and external devices asynchronously. The dialog in FIG. 7A works in concert with the dialog in FIG. 6D, which illustrates Top, Bottom and Home Z-positions.

FIG. 7A also shows an External Shutter 714 selection. Illustrated at 716 is an exemplary user's selection that a high-speed wavelength changer, the Sutter DG4, can serve as the external shutter for camera 330. Recall that in FIG. 6B, a user may elect to keep the camera shutter open during the entire exposure time. The External Shutter 714 selection works in concert with the dialog in FIG. 6B to direct a highspeed wavelength changer to function as an external shutter.

Figure 7B:
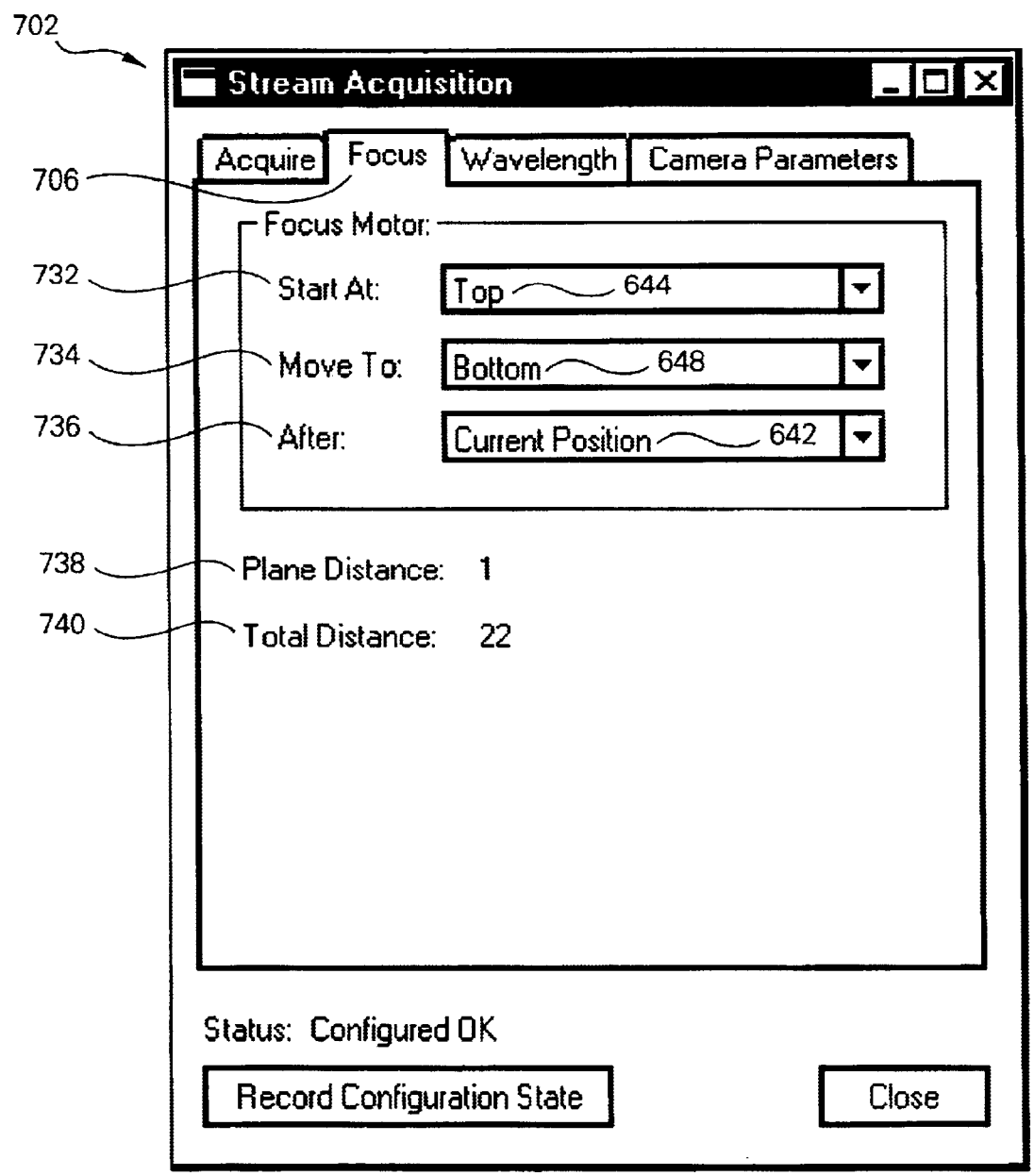
FIG. 7B shows the Focus user interface dialog of the Stream Acquisition embodiment of the present invention by which a user may input the starting and final focus position of an installed objective lens positioner.

FIG. 7B shows the Focus 706 dialog in which a user may select the starting and final Z-position of objective lens 324 as well as the direction in which piezofocuser 340 moves during acquisition. The Focus 706 dialog works in concert with FIG. 6D wherein the Top 644, Home 646, Bottom 648 and Current 642 positions are input. As illustrated in FIG. 7B, at the start of image acquisition 732, piezofocuser 340 is at the Top 644 of the selected range, 646 (FIG. 6D). During image acquisition 734, piezofocuser 340 moves objective lens 324 downward towards the Bottom of the range, 648 (FIG. 6D). After image acquisition, piezofocuser 340 moves the lens 324 to the Current Position, 642 (FIG. 6D), which for this example corresponds to Home as illustrated in 646 (FIG. 6D).

FIG. 7B also shows the Plane Distance 738 to be an exemplary 1, which corresponds to the Move Increment 640 option in FIG. 6D. Further, the Total Distance 740, exemplified as 22, corresponds to the total distance calculated in the discussion above of FIG. 6D.

Figure 7C:
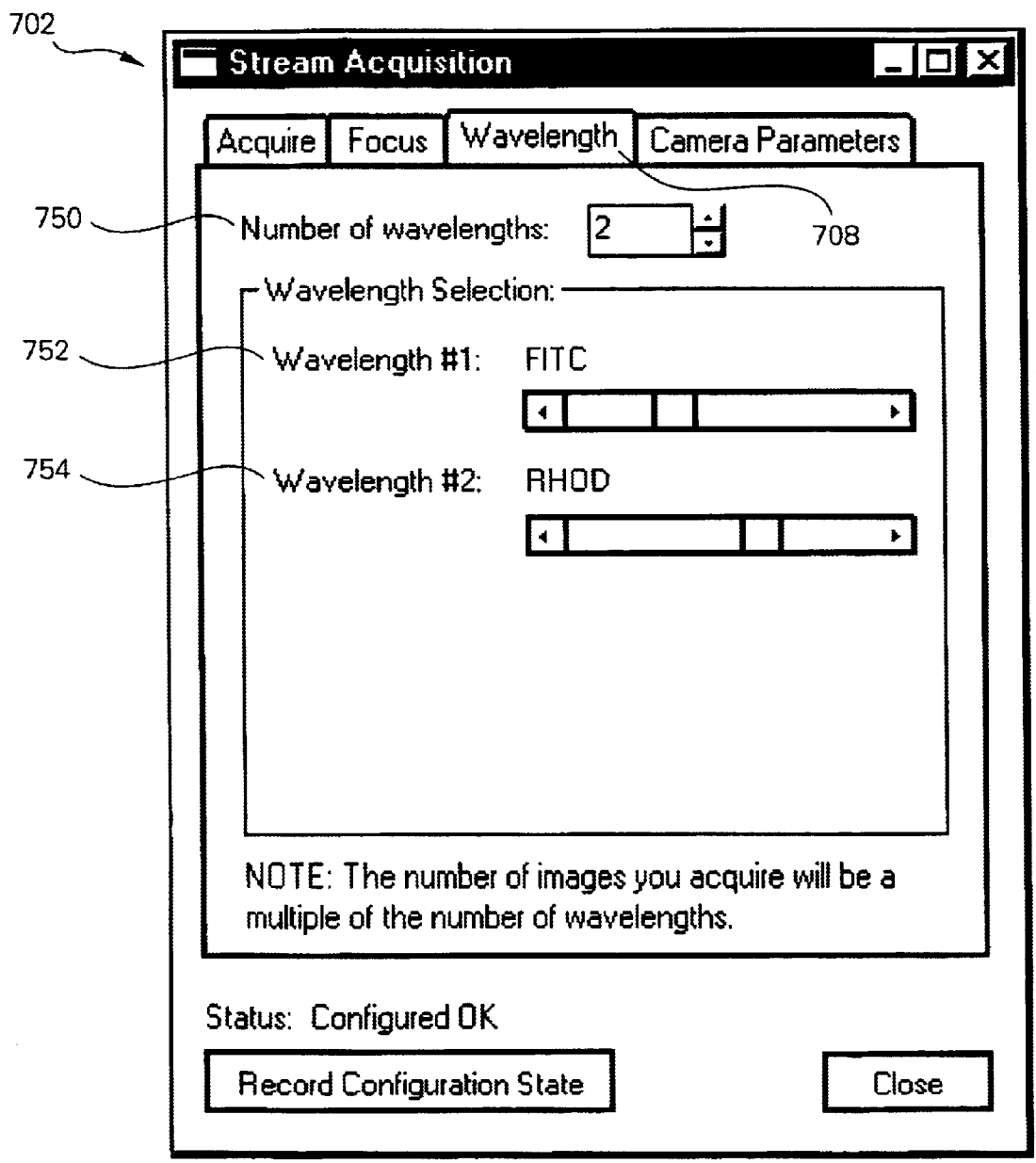
FIG. 7C shows the Wavelength user interface dialog of the Stream Acquisition embodiment of the present invention by which a user may input the wavelengths used to illuminate the specimen during image acquisition.

FIG. 7C shows the Wavelength 708 dialog for the Stream Acquisition 702 embodiment of user input. As exemplified here, a researcher has opted at 750 that the configured wavelength changer, as shown installed at 638 in FIG. 6C, will switch between 2 wavelengths during image acquisition. The exemplary wavelengths include FITC at 752 and RHOD at 754.

FIG. 7D shows the Camera Parameters 710 dialog. In selecting an Acquisition Mode 760, a researcher may choose between different embodiments of a method of the present invention. For example, a researcher may choose to direct camera 330 to acquire images at its frame rate 762, that is, once the shutter is opened, exposure occurs at the maximum operation rate of the camera. In an alternative embodiment, the researcher may opt to direct the camera to acquire images on an external trigger 764.

Further, in a different embodiment, a researcher may opt under certain circumstances to direct camera 330 to expose an image only for certain frames, done by inputting a Number of frames to skip, 766. Directing camera 330 to skip frames is useful when the researcher is using an external device 340, 336, 316 and/or 320 that is slower than the read out rate of the configured camera. Because such external devices 340, 336, 316 and/or 320 are changing the Z-position and wavelength as camera 330 is exposing the image, the acquired stack will display as garbled. An example of a system configuration when this embodiment of the method would be useful is when a researcher is using a full frame CCD camera and a filter wheel, not a highspeed wavelength changer, to change wavelengths.

For example, by opting to have camera 330 skip 3 frames at 766, a researcher is in effect directing the devices to change the Z-position and/or the wavelength only on every fourth frame. If the rate of exposure and read out for the camera used in the system were 25 ms and the rate of operation of the selected wavelength changer were, for example, 75 ms, opting to skip the devices changing parameters to every fourth frame would give wavelength changers 316 and/or 320 the time necessary to change the wavelength respectively.

MultiDimensional Acquisition Embodiment

With continuing reference to FIG. 5, at step 502 a researcher may choose an alternative embodiment as shown in FIGS. 8A–G for inputting values for various acquisition conditions. This is termed the MultiDimensional Acquisition 802 Embodiment. The distinguishing feature between the MultiDimensional Acquisition 802 embodiment and the Stream Acquisition 702 embodiment is that the MultiDimensional Acquisition 802 embodiment allows the researcher to acquire sets of images of the same specimen using the same acquisition conditions at regular time intervals. The purpose of acquiring images under the same conditions at different time intervals is to create a time lapse video.

Figure 8A:
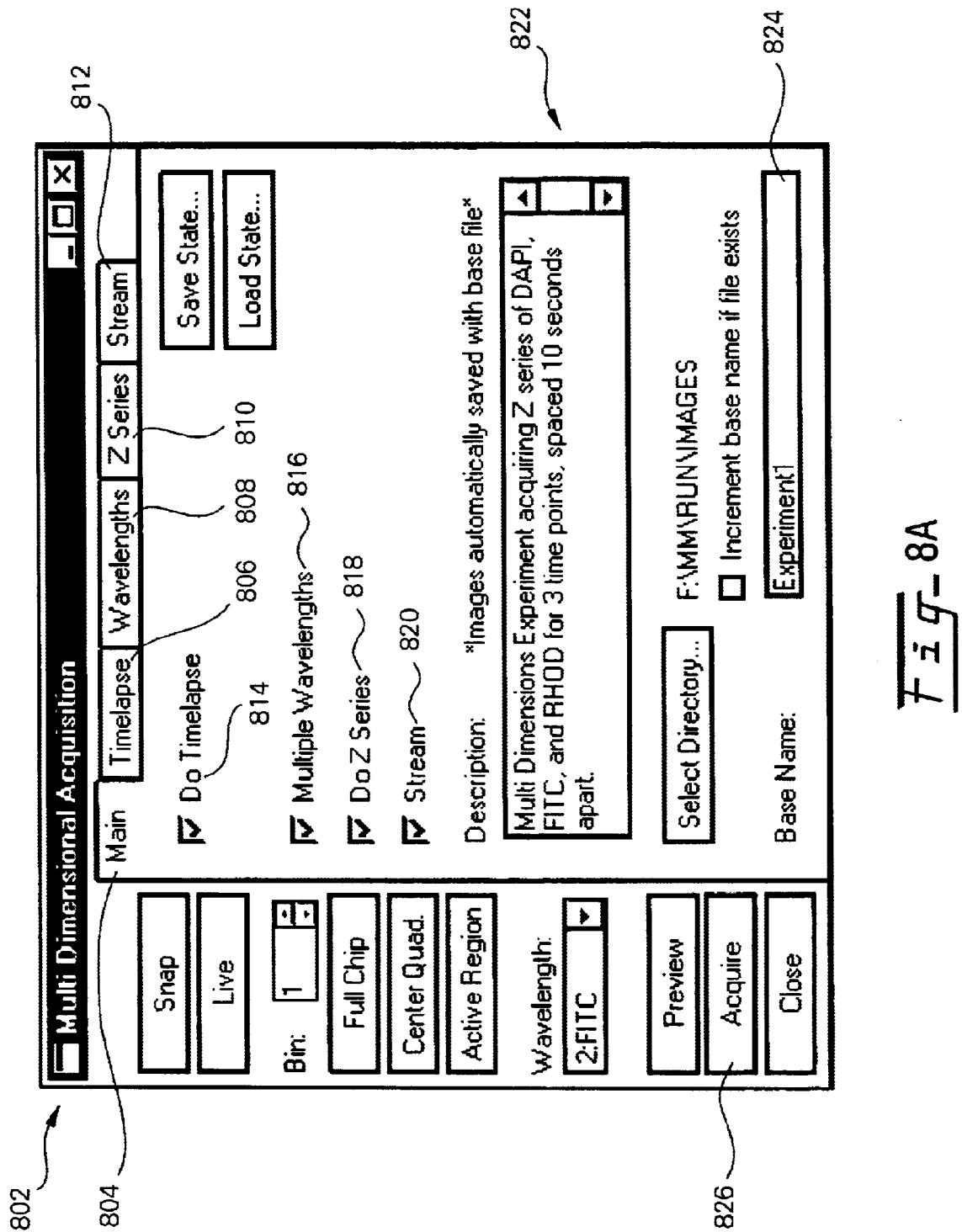
FIG. 8A shows the Main user interface dialog of the MultiDimensional Acquisition embodiment of the present invention.

FIG. 8A shows the Main 802 user dialog of the MultiDimensional Acquisition 802 embodiment. The researcher must have checked each of the acquisition conditions—Timelapse 814, Multiple Wavelengths 816, Do Z Series 816 and Stream 820—as shown in order for the corresponding dialogs of dialogs—Timelapse 806, Wavelengths 808, Z Series 810 and Stream 812 to appear and be accessible to the researcher.

FIG. 8A also shows a Description box 822 in which a researcher may input a file title for the acquired set of images that will be stored identified in permanent memory. As shown, the Description box 822 illustrates that images in the exemplary experiment will be acquired at three separate points in time, 10 seconds apart, as piezofocuser 340 changes the Z-positions and as wavelength changer 316 and/or 320 switches between 3 wavelengths. At Box 824, a user-identified name may be input for the stored file that holds the acquired stack of images.

Figure 8B:
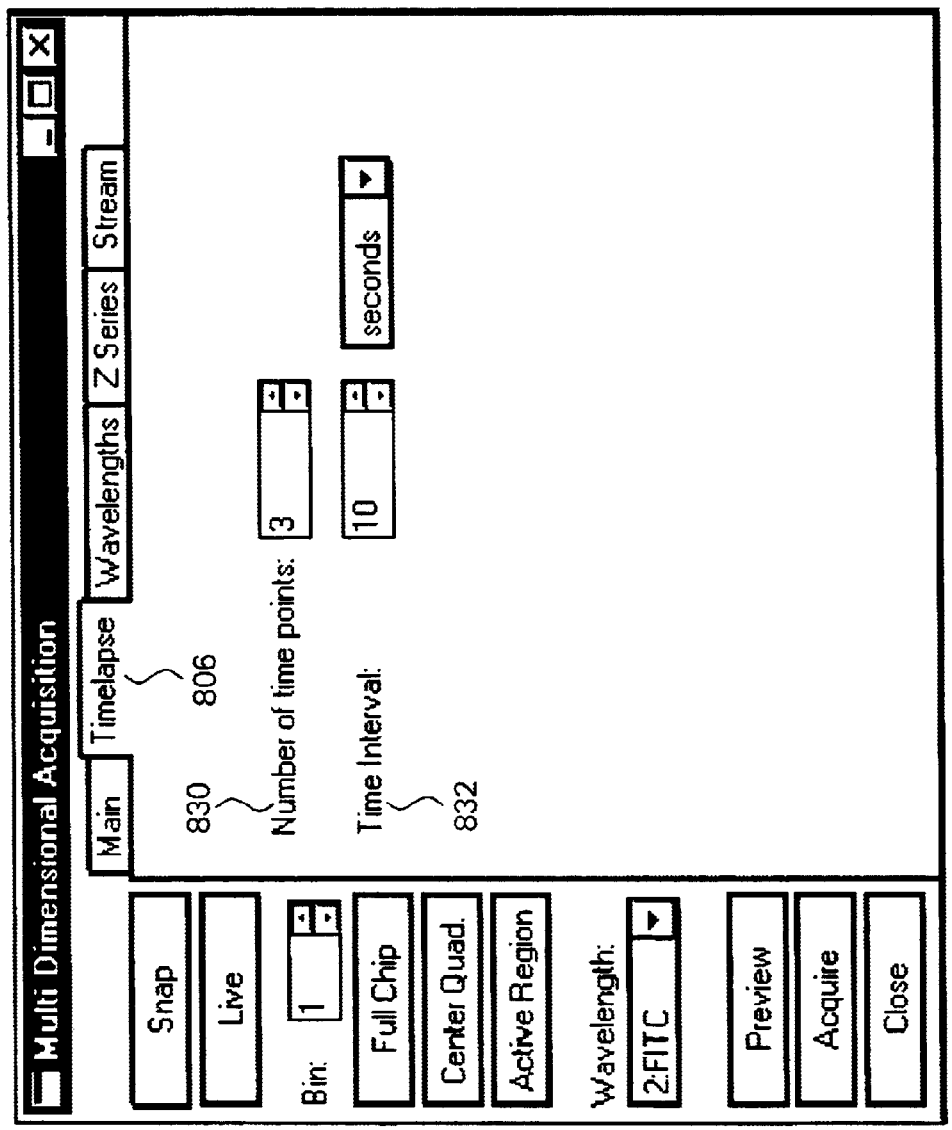
FIG. 8B shows the Timelapse user interface dialog of the MultiDimensional Acquisition embodiment of the present invention by which a user may input the number of times a method of the present invention will acquire images in any one acquisition event.

The Timelapse 806 dialog in FIG. 8B allows a researcher to input the "Number of time points" 830, here shown as 3, as well as the "Time Interval" 832, here shown as ten seconds.

Figure 8C:
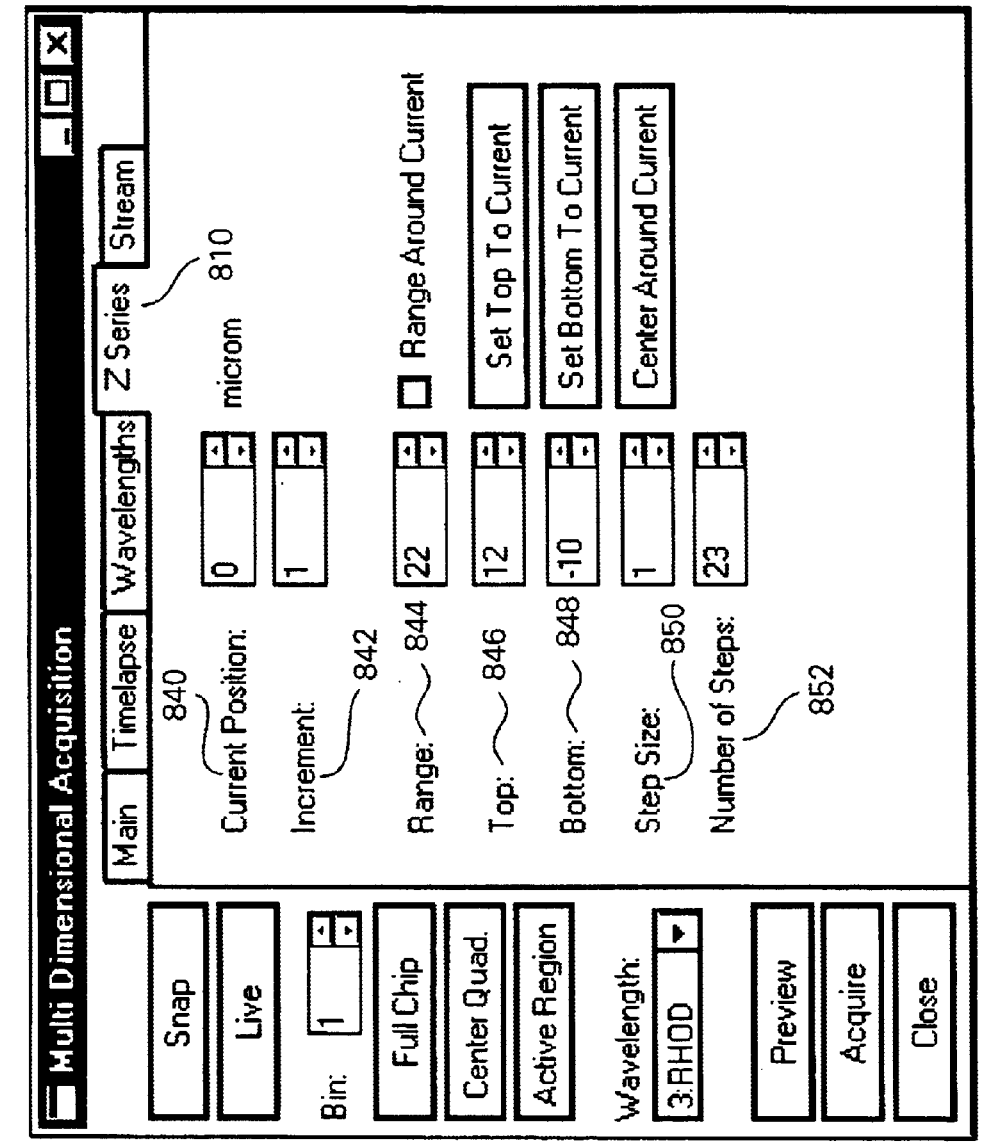
FIG. 8C shows the Z Series user interface dialog of the MultiDimensional Acquisition embodiment of the present invention by which a user may input values for varying the Z-position while performing a method of the present invention.

FIG. 8C shows that upon opening the Z Series 810 dialog, a researcher can input all the pertinent information the program module needs to direct piezofocuser 340 to change Z-positions during image acquisition. This information includes the Current Position 840 of piezofocuser 340, the Increment 842 by which the program module will direct the piezofocuser 340 to move to the next Z-position, the Top 846 and Bottom 848 distances from the Current Position 840, the Step Size 850 and total Number of Steps 852 the piezofocuser 340 will take during image acquisition. The Z dialog 810 allows a more direct inputting of Z Series information than is done in the Stream Acquisition 702 embodiment as well as calculates directly the total Range 844 over which piezofocuser 340 moves objective lens 324 during image acquisition. Specifically, the MultiDimensional Acquisition 802 embodiment uses the 810 dialog to input the same Z series information as is input in the two dialogs shown in FIG. 7B and FIG. 6D under the Stream Acquisition 702 embodiment.

Figure 8D:
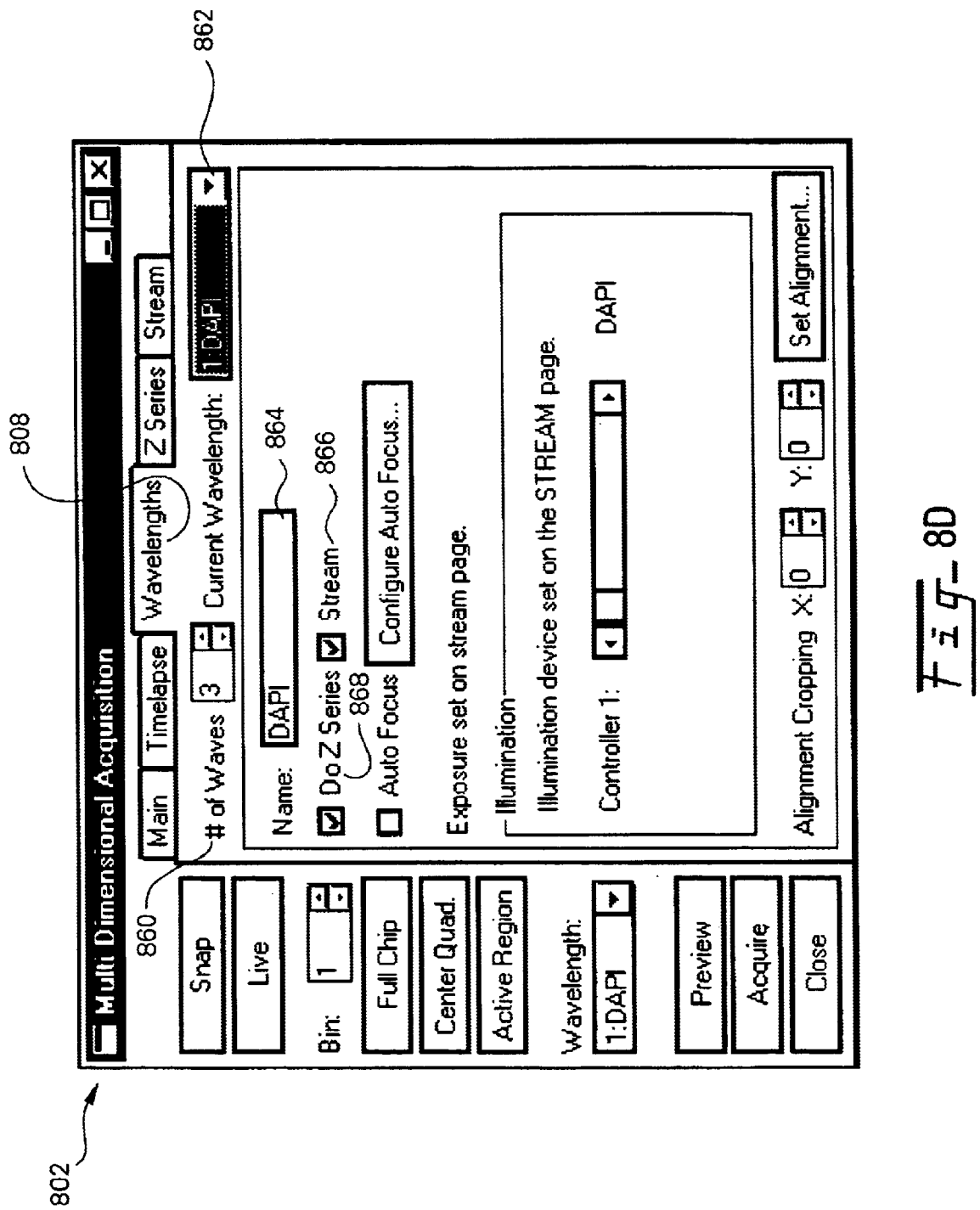
FIGS. 8D–F show the Wavelengths user interface dialog of the MultiDimensional Acquisition embodiment of the present invention by which a user may input values for varying the wavelength while performing a method of the present invention.
Figure 8E:
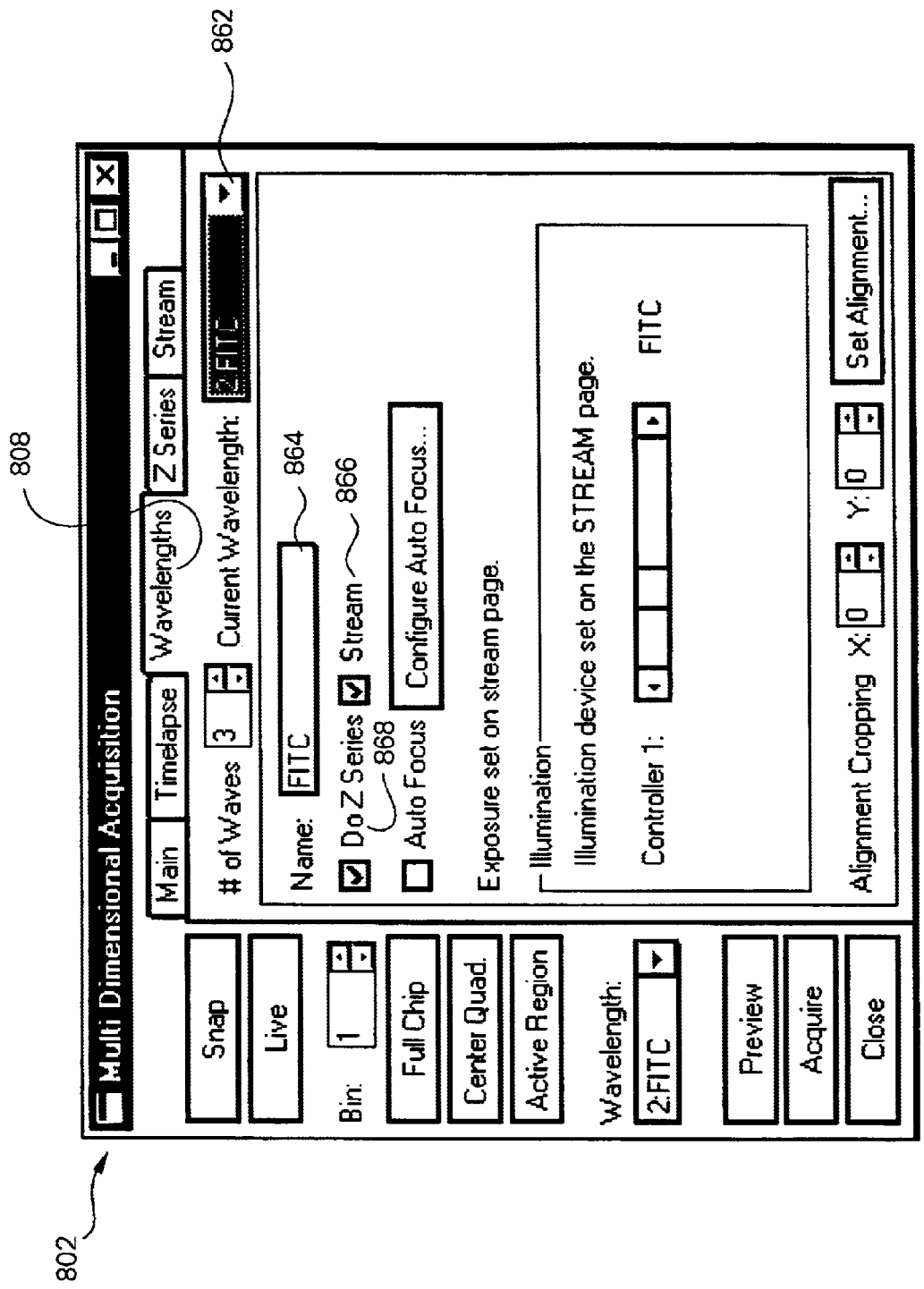
Figure 8F:
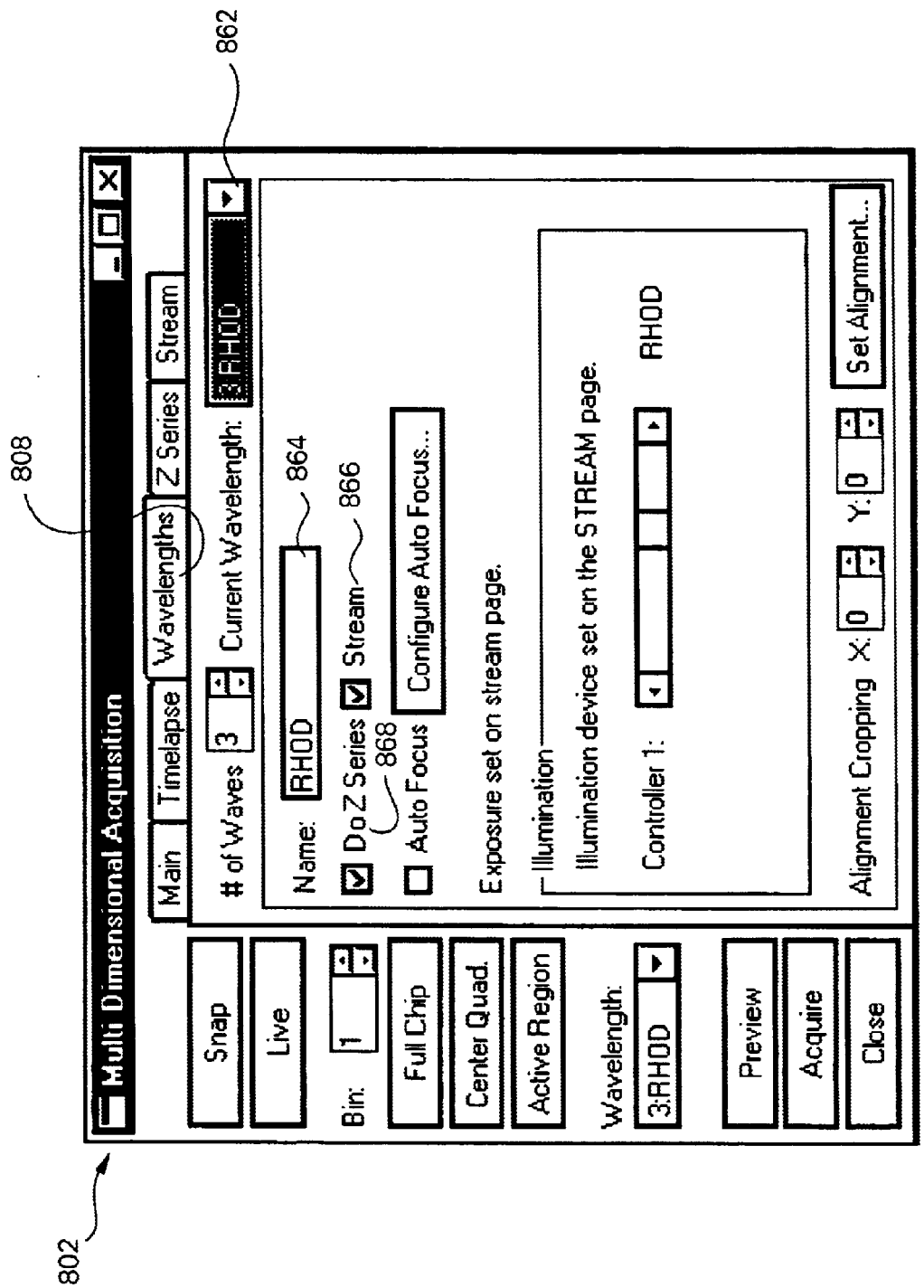

FIGS. 8D–F show the Wavelengths 808 dialog. A researcher can specify in the # of Waves 860 box a maximum of 8 wavelengths that can be switched between while camera 330 is acquiring images. As illustrated here, 3 wavelengths have been selected. A researcher may type in a unique name for each numbered wavelength in the Name 864 box. The Current Wavelength 862 box will indicate the list of input wavelength names and which wavelength the program module has directed wavelength changer 316 and/or 320 to start illuminating with when camera 330 starts exposing.

In FIG. 8D, the Current Wavelength 862 is listed as 1:DAPI; in FIG. 8E, as 2:FITC; and in FIG. 8F, as 3:RHOD. The names DAPI, FITC, and RHOD refer to abbreviations for fluorescent stains known in the art, each of which has a distinctive emission color when excited by a certain wavelength. Therefore, identifying a wavelength with the name of a fluorescent stain that will become especially visible upon illumination by that wavelength gives a researcher an easy mnemonic for identifying various wavelengths. When inputting wavelength names, a researcher must associate an order with a specific name. That is, each input wavelength is given a number that indicates the order in which it will illuminate during acquisition. In this way, by keying in and assigning an order to each wavelength, the program module can create a wavelength table.

When the user has configured a piezofocuser and a wavelength changer that operates fast enough so that the program module can direct these devices to change Z-position and wavelength as the camera is acquiring images, fields 866 and 868 appear checked as shown in FIGS. 8D–F. In effect, the checks at 866 and 868 give notice and confirmation to the user that system 300 is configured with camera 330 and external devices 340, 336, 316 and/or 320 that can be used to perform the method of the present invention.

Figure 8G:
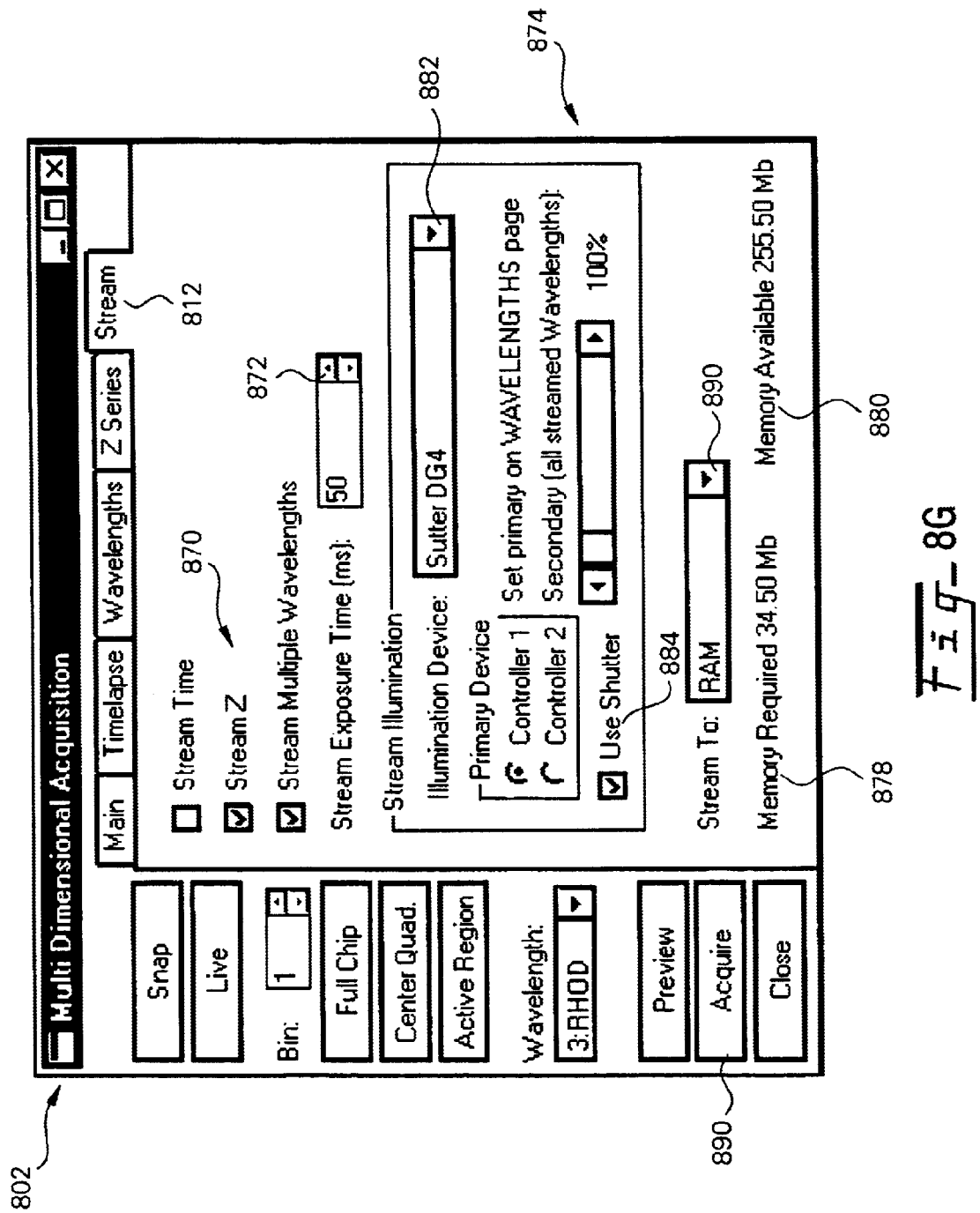
FIG. 8G shows the Stream user interface dialog of the MultiDimensional Acquisition embodiment of the present invention.

FIG. 8G shows the Stream 812 dialog, which, to reiterate, appears only if the user has clicked on the Stream 820 option in the Main 804 user dialog. Clicking on this option and configuring the system with an appropriate camera and external devices notifies the information handling system 200 that the method of the present invention may be invoked, thus it serves as a further notice to the user. At heart, dialog 802 serves to give the researcher a single-page summary of the system parameters or dimensions that the method will execute after the researcher has initiated image acquisition. Shown at field 870 is a list of dimensions that will be varied during image acquisition, which as illustrated are the Z-position and wavelength.

At box 872, the Exposure Time of the entire Acquisition duration is illustrated as 50 ms. The Stream Illumination 874 box allows the researcher at 882 to select from a list of configured wavelength changers, which may be used to vary wavelength during acquisition. As illustrated, a Sutter DG4 has been selected.

At 876, the researcher can select which memory location the digitized images will be temporarily stored during acquisition, illustrated here as RAM.

Memory Allocation

With continuing reference to FIG. 5 and FIG. 7A, after a researcher has input the required acquisition information, the program module determines at step 504 whether the information handling subsystem 200 contains enough temporary memory to acquire and store the requested stack(s) of images. In the Stream Acquisition 702 embodiment, the Acquire 704 dialog in FIG. 7A shows at 722 the memory requirements for an exemplary stack. As illustrated at field 728, the Total number of frames in the exemplary stack will be 46 and the amount of temporary memory 722 needed to store the 46 frames will be 23.00 Megabytes. The Amount of memory available 724 is exemplified as 255.50 Megabytes. The researcher is thereby notified that the system contains enough temporary memory to acquire the. exemplary stack of 46 images given the system parameters as configured in FIGS. 7A and B.

With continuing reference to FIG. 8G, in the MultiDimensional Acquisition 802 embodiment of user input, the researcher is informed at field 878 of how much. temporary memory the exemplary stack will demand, illustrated as 34.50 Megabytes, and at field 880 how much memory is available in the exemplary information handling system, illustrated as 255.50 Megabytes.

Initialization

With continuing reference to FIGS. 1, 3 and 5, once the system has been configured, specific values input and memory allocation performed, the program module at step 506 directs computer 211 to determine if the Z-position will be varying during stream acquisition. If so, in step 508, the program module initializes the starting Z-position by moving piezofocuser 340 or stage mover 336 to the position specified by the user as the Start Position. For the Stream Acquisition 702 embodiment, this is the Start At 732 field in FIG. 7B, which could be either the TOP 644 or BOTTOM 648 position as illustrated in FIG. 6D. For the MultiDimensional Acquisition 802 embodiment, refer hereinabove to the discussion of elements 846 and 848 in FIG. 8C. At step 509, the program module creates a table of Z positions, discussed above in the description of FIG. 8D.

At step 510, the program module directs computer 211 to determine if the wavelength will be varying during stream acquisition and if so, to move the wavelength changer 316 and/or 320 to the position selected by the user as position 1 in step 502. For the Stream Acquistion 702 embodiment, this is the Wavelength #1 field, element 752 in FIG. 7C. For the Multi-Dimensional Acquisition 802 embodiment, refer above to the discussion of element 862 in FIG. 8D.

In step 513, the program module creates a table of wavelength values that specifies the order in which the- .wavelength changer 316 and/or 320 will switch the wavelengths, which relates back to the discussion of element 862 in FIGS. 8D–F.

In step 514, the program module initializes camera 330 by setting its frame number to zero and determines in step 516 whether camera 330 has an external shutter 314. If so, the program module opens the external shutter in 518, and in step 520 directs the camera to wait a certain delay period to assure that the shutter has opened before starting to acquire images. The duration of such delay depends on the particular shutter.

Image Acquisition

At step 522, the system is ready to begin acquiring images. Once the researcher initiates the acquisition routine, the camera starts to acquire images while and as the external devices operate asynchronously to vary the Z-position and/or the wavelength. For the Stream Acquisition 702 embodiment, FIG. 7A shows the Acquire 732 button by which the acquisition routine is initiated. For the MultiDimensional Acquisition 802 embodiment, the Acquire 826 button is shown in FIG. 8A.

The Acquire routine of step 522 is more fully depicted in FIGS. 9 and 10 and described hereinbelow. A summary of step 522 is the following: as an exposed frame is read out from camera 330 into a temporary memory location of computer 211, the program module of the present invention directs the Z-position and/or wavelength to increment to the next position. The camera then exposes the next frame, thereby capturing an image that will show the changed Z-position and/or wavelength. During read out of that frame, the program module again directs the incrementing of the Z-position and/or wavelength. After read out of the last frame, the program module ends acquisition of the stack.

After all the images have been read out and stored, in steps 524–526 the program module directs external shutter 314—if employed during acquisition—to close. In step 528, the stack of acquired images is copied out of the temporary memory location into a more permanent system memory location, thereby freeing system memory resources in 530 to begin another acquisition event, if so desired, or ending the process at 532.

Different embodiments of the system of the present invention will store the acquired images in different temporary memory locations. In one embodiment employing a personal computer as the processor, a temporary memory location may comprise a buffer in the RAM of the computer. Other system embodiments may store the acquired images on a real time hard disk, which may include a Redundant Array of Inexpensive Drives (RAID), or other computer readable medium or, for embodiments using a distributed computing environment or for embodiments where access to the program module is achieved via the Internet, on a local or remote server. Moreover, different embodiments of the present invention may store the acquired images in different permanent memory locations. Those skilled in the art will appreciate that different embodiments of the optical microscope system 100, especially as they relate to using different computer configurations 211 for processing the acquired images, may employ a variety of permanent memory locations for storing the images.

Asynchronous Operation of Camera and External Devices During Image Acquisition

With continuing reference to FIGS. 2 and 3, FIGS. 9 and 10 show more in detail the sequence of steps for acquiring images by camera 330 operating at or near its maximum rate while and as external devices 340, 336, 316 and/or 320 operate asynchronously with the camera. At step 900 in FIG. 9 the user initiates the Acquire routine of the program module, the whole of which corresponds to step 522 in FIG. 5. At step 902, the program module resets the frame number of the system to be 0. At step 904, the program module begins the steps of image acquisition.

At this point, the method of the present invention bifurcates into two interrelated lines of processing, one line performed by camera 330 and represented by steps 912 to 916 and 922 to 928. The grey-filled shading of the nodes at these steps indicate camera controller processing. The second interrelated line relates to processing done within the main computer and comprises the steps of 918, 932, 936, 938 and 940. Steps 932, 936, 938 and 940 are performed by the main processor and are so indicated by nodes with diagonal lines; step 918 is performed by the software interrupt handler, which is so indicated by cross-hatching.

Image Acquisition and the Software Interrupt

At step 912, the program module informs camera 330 of the total number of frames that the researcher has requested—equal to the number of Z-positions multiplied by the number of wavelengths (See discussion of FIG. 7A)—and directs the camera to begin exposing the first frame. Simultaneously, computer 211 begins its line of processing at step 932, which is to determine whether the frame number has incremented.

Between the time that step 912 is finishing and before read out begins at step 916, computer 211 is alerted that the exposure is ending by receiving a software interrupt-an instruction that halts computer 211 from its continuous processing of the frame number. This alerting step occurs at node 914. At step 918, a software interrupt handler, which is a script in the Acquire routine of the program module, notifies computer 211 to update the frame number, which is denoted by the broken line 919 connecting node 918 and node 932. Once computer 211 increments the frame number by 1, it returns to loop 933, where most of its processing time is spent waiting for the frame number to increment.

At step 916, read out of the exposure image begins to a temporary memory location, for example, RAM, via Direct Memory Access (DMA). With reference to FIG. 1, DMA is the method whereby the camera interface card 225 resident in computer 211 can transfer image data from camera 130 directly into the memory of computer 211 without requiring the intervention of application software 245.

At this point, the program module can move through different embodiments of the method depending on the configured camera. If the researcher has configured a frame transfer CCD camera or an interline CCD camera operating in overlapped mode into the system, then the program module progresses directly to step 926 while the exposed image of the current frame is still being read out to temporary memory.

This embodied pathway depends on the special structure of these cameras. As discussed hereinabove, the CCD device of a frame transfer camera has an architecture that allows a current frame to be acquired while the previous frame is being transferred to temporary memory. Specifically, the frame transfer CCD device comprises both an imaging area of photodiodes and a masked area, whereby the exposed image of the previous frame is transferred very rapidly from the imaging photodiode area to the masked area. The imaging area of the camera is thus freed to begin exposing an image in the current frame before the previous image is read out completely to temporary memory. In effect, the masked photodiode area represents a kind of stopgap storage by which the camera can overlap the function of exposure with the function of read out. The overlapping of these two functions results in very rapid image acquisition. An interline CCD camera operating in overlapping mode functions similarly as a frame transfer camera and consequently has the same rapid rate of image acquisition. The image acquisition rate of various models of these kinds of digital cameras is not standardized as with video cameras. For example, one frame transfer camera model listed in the Specific Apparatus section hereinabove, the PentaMax line, available from Princeton Instruments, has a frame transfer time of about 1.5 ms.

Alternatively, if the acquiring camera is not a frame transfer CCD or an interline CCD camera operating in overlapped mode, the program module moves through a different embodiment of the method. That is, before moving on to step 926, the program module executes step 924 by waiting for the exposed image of the current frame to be completely read out. This pathway is employed when, for example, a full frame CCD camera constitutes the configured camera in the system.

The structure of the specific camera also has implications for how the software interrupt is generated in step 914. The method of the present invention requires that the camera controller or the PCI interface card 225 be capable of alerting computer 211 in the transition period after the exposure has completed and read out is commencing. In the case of digital cameras, the camera controller so alerts computer 211 by generating a software interrupt at the appropriate transition moment. Different camera manufacturers may term the transition moment differently. For example, Roper Scientific, which manufactures the Princeton Instruments and Photometrics lines of scientific grade digital cameras, terms this transition moment as Beginning of Frame or BOF, and defines it as the start of read out.

In order for a software interrupt to be generated when video cameras conforming to the RS-170 or CCIR monochrome or RGB specifications are configured into the system, a PCI digitizer card (225 in FIG. 1) or frame grabber must be configured into the system and be capable of generating a signal in the form of a software interrupt when the frame grabber has completed digitization of the current frame. At completion of digitization of a frame, an event known in the art as a vertical blank, or v-blank, is generated. Integral Technologies, manufacturer of the FlashBus MV-Pro frame grabber card, has implemented a software interrupt when the v-blank occurs. Other manufacturers of frame grabber cards may also generate a software interrupt for this event. The method of the present invention uses the software interrupt, generated either at the BOF of a digital camera or the v-blank of the video frame grabber, as the signal for alerting the computer 211 method that camera 330 has completed exposure of one frame.

After the program module has moved to step 926, the camera determines whether the last frame has been exposed. If so, the camera ends acquisition in step 928. If not, the camera continues and exposes the next frame.

Changing the Z-Position and/or Wavelength and the Software Interrupt

Figure 9:
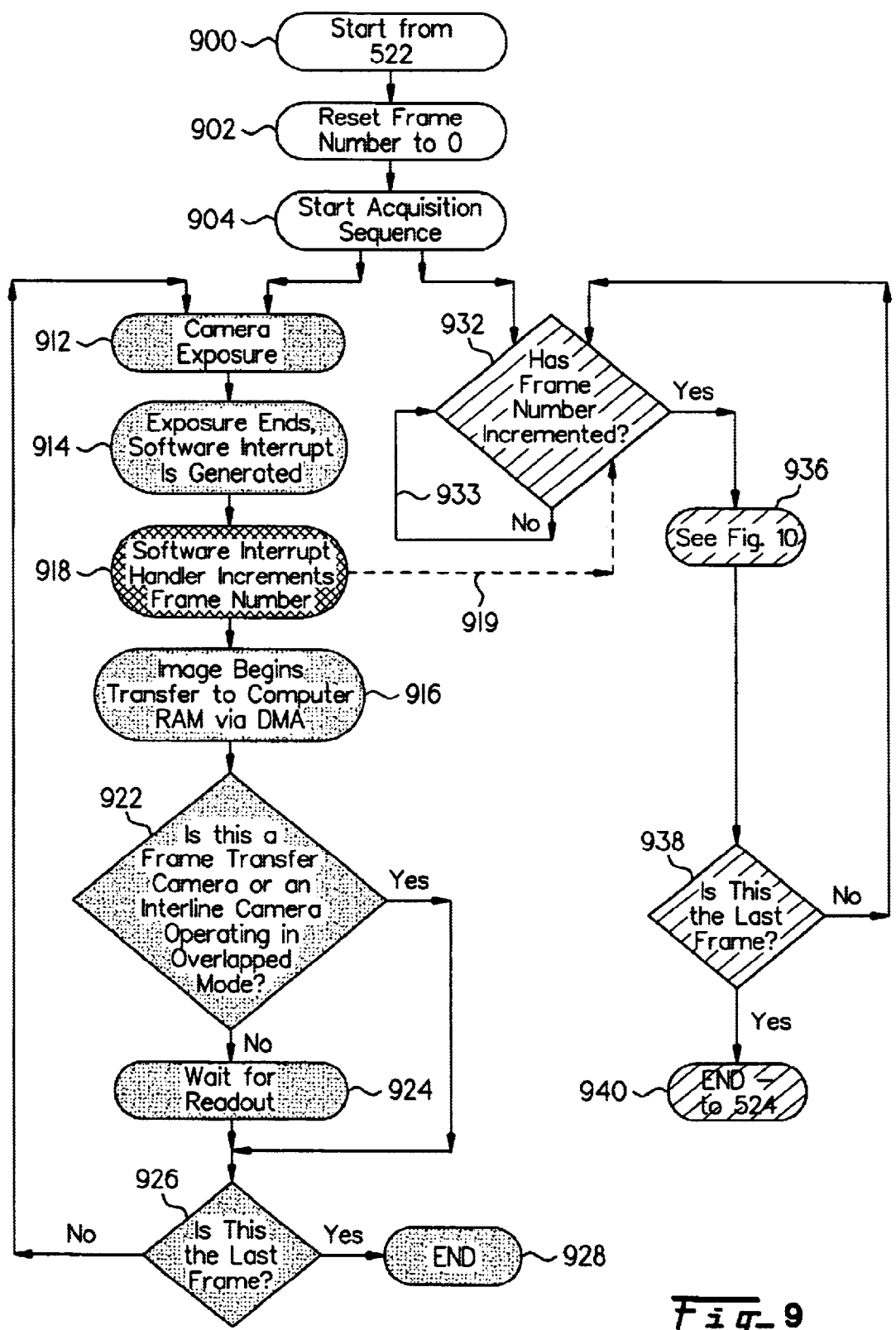
FIG. 9 is a flow chart diagram depicting an exemplary embodiment of the steps of the Acquire routine of the present invention for directing a camera operating at or near its maximum rate to acquire images while and as external devices operate asychronously with the camera.

With continuing reference to FIG. 9, a critical point to grasp in the method of the present invention is that step 916 and step 936 are co-occurring. That is, as the camera controller, in step 916, is transferring the exposed, digitized image to a memory buffer of computer 211, the program module in step 936 is executing the routine shown in FIG. 10. Recall that in step 918 the software interrupt handler, a script in the program module, causes the frame number to be incremented. Upon receiving a software interrupt from the camera controller or video frame grabber in step 914, the software interrupt handler interrupts, through pathway 919, the processing subroutine 933 of system computer 211 to notify the computer to increment the frame number by 1. With the updating of the frame number at step 932, the program module proceeds to step 936, which is the routine executed in FIG. 10.

Figure 10:
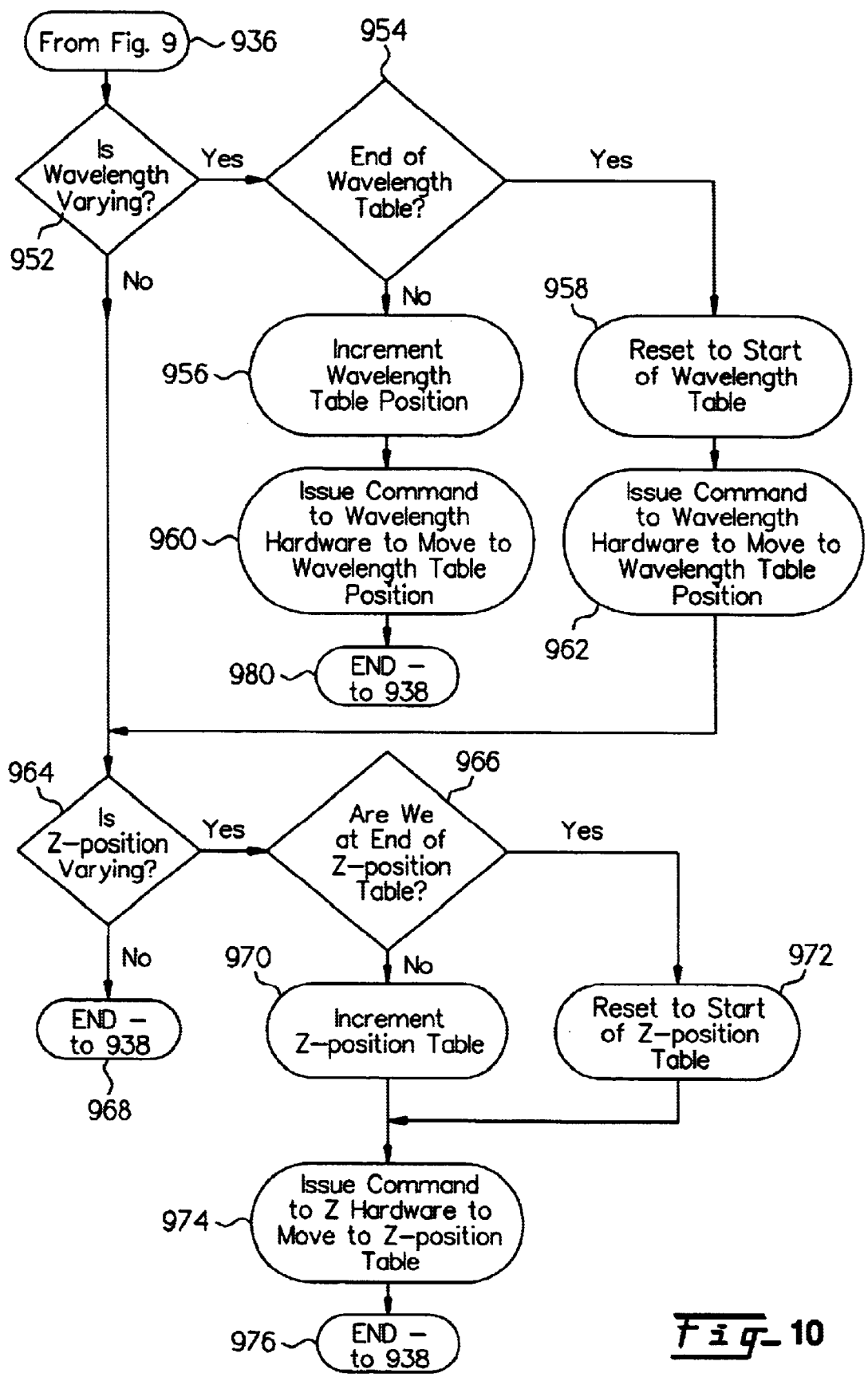
FIG. 10 is a flow chart diagram depicting an exemplary embodiment of the steps of a method of the present invention for directing external devices to vary image acquisition parameters while and as these devices operate asychronously with the camera.

To summarize, step 936 as shown in FIG. 9 comprises the routine shown in FIG. 10 for varying the Z-position and/or wavelength, which is executed by computer 211 at the same time that camera 330 is executing steps 916 through 924 in FIG. 9. The co-occurrence of step 936 with steps 916 through 924 constitutes the asynchronous operation of the camera with the external devices.

In FIG. 10, at step 952 the program module queries if the system will be varying the wavelength during acquisition. If not, the program module moves to step 964 to determine whether the Z-position will be varying during acquisition.

If the system has been configured to vary wavelength, either under the Stream Acquisition 702 embodiment as illustrated in FIG. 7C or under the Multi-Dimensional Acquisition 802 embodiment as illustrated in FIGS. 8D–F, at step 954 the program module queries whether the illuminating wavelength for the last frame was the last one listed in the wavelength table. If not, in steps 956 and 960, the program module directs the wavelength changer 316 and/or 320 to change the wavelength to the next one listed in the Wavelength Table. At this point, the method goes back to step 938 in FIG. 9, at which point the program module determines whether to execute a new exposure at the changed wavelength or to end acquisition.

Alternatively, if the wavelength for the last frame were the last one listed in the Wavelength Table, in steps 958 and 962, the program module directs the wavelength changer 316 and/or 320 to change the wavelength to the one listed at the start of the table. This means that, at this particular Z-position, each of the selected wavelengths has illuminated the image in different frames.

At this point, the method progresses to step 964 where the program module queries whether the Z-position will be varied during the acquisition of this stack of images. If no, at step 968 the method reverts back to step 938 in FIG. 9, wherein the program module determines whether the last frame has been acquired.

If the Z-position is varying during this acquisition event, at step 966 the program module determines whether to change the value of the Z-position. If objective lens 324 or stage 326 is already at the last value listed in the Z-position table, in step 972 the program module resets the next Z-position to be the first value in the table. Alternatively, if the last value in the Z-position table has not been reached, the program module in step 970 increments the value of the Z-position by 1. In step 974, the program module directs piezofocuser 340 or stage mover 336 to move to the next Z-position. At step, 976 the method then reverts back to step 938 in FIG. 9.

Here the program module determines whether this was the last frame. If not, the program module increments the frame number by 1 at step 932 and re-enters, at step 936, the routine of FIG. 10 to again change the wavelength and/or the Z-position. The routine of FIG. 10 is performed until the program module determines at step 938 that the last frame has been exposed.

As discussed above in regards to the MultiDimensional 802 embodiment of user input, a researcher may select to acquire a set of images at different points in time. If different time series are selected, as illustrated at field 830 in FIG. 8B as 3, the program module will calculate the number of frames as equal to the number of Z-positions times the number of wavelengths times the number of time points. Thus, to continue with the above example, for 23 Z-points and 3 wavelengths and 3 time points, the total number of frames equals 23×3×3, or 207 frames.

At step 940, the program module ends the Acquire routine and the method progresses to step 524 in FIG. 5. As discussed hereinabove in the description of FIG. 5, the method progresses from steps 524 through 530, which comprise closing the external shutter, if any, copying the stack of images from temporary to permanent memory, thereby freeing temporary memory and completing the method.

Post-Acquisition Processing

After all the images have been acquired and stored in permanent memory, the method has been completed. However, after the completion of the method, a researcher can then process the acquired stack in a variety of known ways by suitable application software to create observations that previously have not been possible to make. For example, a very important and valuable way of processing the acquired stack is to play it back as an uninterrupted sequence of images, that is, as a "movie", that shows the variation in focus plane and illuminated light as continuous.

Figure 11:
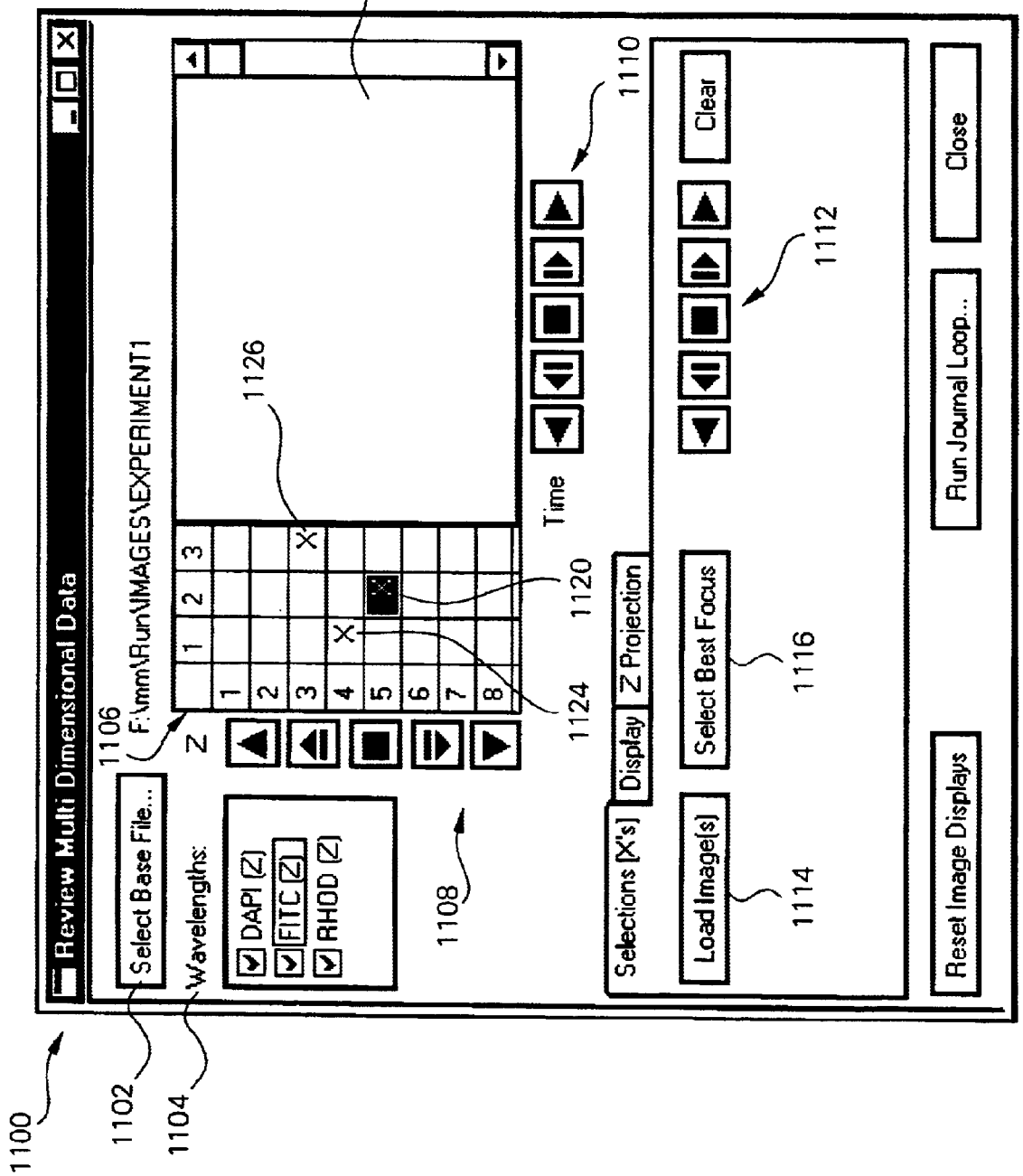
FIG. 11 shows the Review MultiDimensional Data user interface dialog of an exemplary image processing software application by which a user can playback a sequence of images created by a method of the present invention as a continuous stream or movie.

FIG. 11. shows an example of the Review MultiDimensional Data 1100 user dialog in MetaMorph™, a software application that can process the acquired stack of images, by which a user can select to display the acquired stack of images as a continuous stream, that is, as a movie. Clicking on the Select Base File 1102 button in FIG. 11 allows a researcher to select the file containing the desired stack of images to be processed. Recall that at field 824 in FIG. 8A a researcher can input using the method of the present invention an identifying file name for the acquisition event. Having selected a file, a researcher can request in the Wavelengths 1104 box that the selected file of images display as being illuminated by certain wavelengths. As shown here in 1104, a researcher may check any or all of those illuminating wavelengths that were selected in FIGS. 8D–F, illustrated as DAPI, FITC and RHOD. Each checked wavelength as illustrated in 1104 appear in its own window.

Z table 1106 is a two-dimensional array of all of the frames acquired at selected Z-positions in different time series. The number of columns shown in Table 1106 equals the number of time series input by the user. As illustrated at field 830 in FIG. 8B, the number of time series is 3, which corresponds to the number of columns in Table 1106. The number of rows in Table 1106 corresponds to the number of Z-positions input at field 852 in FIG. 8C, exemplified there as 23. Thus, column 1 in Table 1106 represents the 23 Z-positions acquired during the first time series, column 2 represents the 23 Z-positions acquired during the second time series, and so on.

To view an individual frame acquired at a certain Z-position in a particular time series and illuminated by one of the checked wavelengths in Box 1104, a researcher clicks on a particular cell of Table 1106. The images corresponding to that Z-position for that time series for each wavelength checked in 1104 are displayed in Box 1122. As an example, highlighted cell 1120 corresponds to all the checked wavelengths at the fifth Z-position of the second time series.

To view a movie of all the Z-positions of a certain time series, a researcher highlights a cell in the 1106 array, say in column 1, and clicks on the appropriate arrow buttons at 1108 to play forwards and backwards through the 23 Z-positions of the first time series. To view the images of a certain Z-position through through time, a researcher highlights a certain cell, for example, cell 1120 at the fifth Z-position, and clicks on the appropriate arrow buttons at 1112 to play forwards and backwards through the 3 images of Z-position #5 in the three time series.

Clicking on the Load Images 1114 button collates all the selected frames as a subset of the originally-acquired stack. In this way, the subset stack may be played back as a movie to view the change in that parameter through time. Even more importantly, by clicking on the Select Best Focus 1116 button, a researcher can initiate an autofocusing algorithm for all Z-position images of a certain time series in order to determine which Z-position, in other words, which focus plane, contains the best-focused image. When the algorithm finds the best focus position, an "X" will be placed at that location, as illustrated at 1120. The autofocusing continues until a table of best focus positions for each time series has been created, illustrated by the "X's" at 1120, 1124 and 1126. The researcher can then play these frames using the appropriate buttons at 1112 or click on 1114 to assemble these frames into a subset stack, that can be played back as a movie of the best focus positions throughout time.

Although this discussion of post-acquisition processing of a stack of frames acquired using the present invention does not describe claimed elements of the present invention, it has been included to explicate how the present invention provides a previously unknown kind of image set which researchers can process in known ways so as to create observations of biological events at the cellular level that could not have been made previously.

Although the invention has been particularly shown and described with reference to certain embodiments, those skilled in the art will understand that various changes in form and detail may be made without departing from the spirit and scope of the invention.

What is claimed is:

1. A method for acquiring images using an optical microscope system comprising the steps of:
   a) configuring an optical microscope system, which comprises a camera, a microscope, an information handling system and at least one device external to the microscope that which operates to vary at least one image acquisition parameter;
   b) acquiring images at a rate substantially close to the maximum image acquisition rate of said camera;
   c) during the acquiring of images, operating at least one said system device at a rate substantially close to the maximum image acquisition rate of said camera, whereby at least one image acquisition parameter is altered and whereby the acquired images display said altering of at least one image acquisition parameter;
   d) storing the acquired images as at least one stack of digitized data images;
   wherein configuring an optical microscope system comprises
      (i) initializing said system so as to input the rate of image acquisition of said camera and to input the rate at which said external devices operate to vary the image acquisition parameters,
      (ii) initializing a range of values over which said image acquisition parameters will vary during the acquiring of images,
      (iii) comparing the operation rate of said external devices in varying said image acquisition parameters with the rate of said camera to determine whether said configured system can acquire images at or near the acquisition rate of said camera while said external devices are varying said image acquisition parameters, (iv) deciding whether said system contains enough memory to store the stack of digitized images that will be acquired while and as said system devices will operate to vary the image acquisition parameters over said range of values.

2. An automated optical microscope system programmed to contain a computer program product that executes the steps of claim 1, comprising:
    a microscope,
    a camera,
    an information handling system comprising a computer and memory,
    at least one means external to the microscope for varying at least one image acquisition parameter.

3. The system of claim 2, wherein the acquired images are stored in Random Access Memory.

4. The system of claim 2, wherein the acquired images are stored in real time hard disks.

5. The system of claim 2, wherein the acquired images are stored on a computer readable medium.

6. The system of claim 2, wherein the acquired images are stored on a server to which said information handling system is connected.

7. The system of claim 2, wherein the processing of the stack of digitized data is done by a computerized image processing method for acquiring and processing images of fluorescently stained cellular elements, whereby said computerized method contains a program module that executes a method which comprises the steps of:
    a) configuring an optical microscope system, which comprises a camera, a microscope, an information handling system and at least one device external to the microscope that which operates to vary at least one image acquisition parameter;
    b) acquiring images at a rate substantially close to the maximum image acquisition rate of said camera;
    c) during the acquiring of images, operating at least one said system device at a rate substantially close to the maximum image acquisition rate of said camera, whereby at least one image acquisition parameter is altered and whereby the acquired images display said altering of at least one image acquisition parameter;
    d) storing the acquired images as at least one stack of digitized data images;
    wherein configuring an optical microscope system comprises
        (i) initializing said system so as to input the rate of image acquisition of said camera and to input the rate at which said external devices operate to vary the image acquisition parameters,
        (ii) initializing a range of values over which said image acquisition parameters will vary during the acquiring of images,
        (iii) comparing the operation rate of said external devices in varying said image acquisition parameters with the rate of said camera to determine whether said configured system can acquire images at or near the acquisition rate of said camera while said external devices are varying said image acquisition parameters,
        (iv) deciding whether said system contains enough memory to store the stack of digitized images that will be acquired while and as said system devices will operate to vary the image acquisition parameters over said range of values.

8. The system of claim 2, wherein a device external to the microscope means comprises a means for varying the vertical position of the objective lens of said microscope.

9. The system of claim 2, wherein a device external to said microscope comprises a means for varying the emission wavelength at which images are acquired.

10. The system of claim 2, wherein a device external to said microscope comprises a means for varying the excitation wavelength at which images are acquired.

11. The system of claim 2, wherein a device external to the microscope comprises a means for varying the vertical position of a stage of said microscope, at which images are acquired.

12. The system of claim 2, wherein all said devices external to the microscope are varying the values of their respective acquisition parameters while and as said camera is acquiring images.

13. A method for acquiring images using an optical microscope system comprising the steps of:
    a) configuring an optical microscope system, which comprises a camera, a microscope, an information handling system and at least one device external to the microscope, which operates to vary at least one image acquisition parameter;
    b) acquiring images at a rate substantially close to the maximum image acquisition rate of said camera;
    c) during the acquiring of images, operating at least one said system device at a rate substantially close to the maximum image acquisition rate of said camera, whereby at least one image acquisition parameter is altered and whereby the acquired images display said altering of at least one image acquisition parameter;
    d) storing the acquired images as at least one stack of digitized data images;
    wherein configuring an optical microscope system comprises:
        (i) initializing said system so as to input the rate of image acquisition of said camera and to input the rate at which said external devices operate to vary the image acquisition parameters,
        (ii) initializing a range of values over which said image acquisition parameters will vary during the acquiring of images,
        (iii) initializing a duration of time during which images will be acquired,
        (iv) comparing the operation rate of said external devices in varying said image acquisition parameters with the rate of said camera to determine whether said configured system can acquire images at or near the acquisition rate of said camera while said external devices are varying said image acquisition parameters,
        (v) deciding whether said system contains enough memory to store the stack of digitized images that will be acquired while and as said system devices will operate to vary the image acquisition parameters over said range of microscope.

14. An automated optical microscope system programmed to contain a computer program product that executes the steps of claim 13, comprising:
    a microscope,
    a camera,
    an information handling system comprising a computer and memory,
    at least one means external to the microscope for varying at least one image acquisition parameter.

15. The system of claim 14, wherein the acquired images are stored in Random Access Memory.

16. The system of claim 14, wherein the acquired images are stored in real time hard disks.

17. The system of claim 14, wherein the acquired images are stored on a computer readable medium.

18. The system of claim 14, wherein the acquired images are stored on a server to which said information handling system is connected.

19. The system of claim 14, wherein processing of the stack of digitized data is done by a computerized image processing method for acquiring and processing images of fluorescently stained cellular elements, whereby said computerized method contains a program module that executes the method which comprises the steps of:

a) configuring an optical microscope system, which comprises a camera, a microscope, an information handling system and at least one device external to the microscope, which operates to vary at least one image acquisition parameter;

b) acquiring images at a rate substantially close to the maximum image acquisition rate of said camera;

c) during the acquiring of images, operating at least one said system device at a rate substantially close to the maximum image acquisition rate of said camera, whereby at least one image acquisition parameter is altered and whereby the acquired images display said altering of at least one image acquisition parameter;

d) storing the acquired images as at least one stack of digitized data images;

wherein configuring an optical microscope system comprises:

(i) initializing said system so as to input the rate of image acquisition of said camera and to input the rate at which said external devices operate to vary the image acquisition parameters, (ii) initializing a range of values over which said image acquisition parameters will vary during the acquiring of images, (iii) initializing a duration of time during which images will be acquired, (iv) comparing the operation rate of said external devices in varying said image acquisition parameters with the rate of said camera to determine whether said configured system can acquire images at or near the acquisition rate of said camera while said external devices are varying said image acquisition parameters, (v) deciding whether said system contains enough memory to store the stack of digitized images that will be acquired while and as said system devices will operate to vary the image acquisition parameters over said range of microscope.

20. The system of claim 14, wherein a device external to the microscope comprises a means for varying the vertical position of the objective lens at which images are acquired.

21. The system of claim 14, wherein a device external to the microscope comprises a means for varying the emission wavelength at which images are acquired.

22. The system of claim 14, wherein a device external to the microscope comprises a means for varying the excitation wavelength at which images are acquired.

23. The system of claim 14, wherein a device external to the microscope comprises a means for varying the vertical position of a stage of said microscope, at which images are acquired.

24. The system of claim 15, wherein all said devices external to the microscope are varying the values of their respective acquisition parameters while and as said camera is acquiring images.

25. A computer program product within a computer readable medium having instructions for acquiring images using an automated optical microscope system, comprising:

instructions within said computer readable medium for configuring an optical microscope system, which comprises a camera, a microscope, an information handling system and at least one device external to the microscope which operates to vary at least one image acquisition parameter;

instructions within said computer readable medium for acquiring images at a rate substantially close to the maximum image acquisition rate of said camera;

instructions within said computer readable medium for operating, during the acquiring of images, at least one said system device at a rate substantially close to the maximum image acquisition rate of said camera, whereby at least one image acquisition parameter is altered and whereby the acquired images display said altering of at least one image acquisition parameter;

instructions within said computer readable medium for storing the acquired images as at least one stack of digitized data images;

wherein the instructions for configuring an optical microscope system comprise instructions for initializing said system so as to input the rate of image acquisition of said camera and to input the rate at which said external devices operate to vary the image acquisition parameters, instructions for initializing a range of values over which said image acquisition parameters will vary during the acquiring of images, instructions for comparing the operation rate of said external devices in varying said image acquisition parameters with the rate of said camera to determine whether said configured system can acquire images at or near the acquisition rate of said camera while said external devices are varying said image acquisition parameters, instructions for deciding whether said system contains enough memory to store the stack of digitized images that will be acquired while and as said system devices will operate to vary the image acquisition parameters over said range of values.

26. A computer program product within a computer readable medium having instructions for acquiring images using an automated optical microscope system, comprising:

instructions within said computer readable medium for configuring an optical microscope system, which comprises a camera, a microscope, an information handling system and at least one device external to the microscope which operates to vary at least one image acquisition parameter;

instructions within said computer readable medium for acquiring images at a rate substantially close to the maximum image acquisition rate of said camera;

instructions within said computer readable medium for operating, during the acquiring of images, at least one said system device at a rate substantially close to the maximum image acquisition rate of said camera, whereby at least one image acquisition parameter is altered and whereby the acquired images display said altering of at least one image acquisition parameter;

instructions within said computer readable medium for storing the acquired images as at least one stack of digitized data images;

wherein the instructions for configuring an optical microscope system comprise:

instructions for initializing said system so as to input the rate of image acquisition of said camera and to input the rate at which said external devices operate to vary the image acquisition parameters, instructions for initializing a range of values over which said image acquisition parameters will vary during the acquiring of images, instructions for initializing a duration of time during which images will be acquired, instructions for comparing the operation rate of said external devices in varying said image acquisition parameters with the rate of said camera to determine whether said configured system can acquire images at or near the acquisition rate of said camera while said external devices are varying said image acquisition parameters, instructions for deciding whether said system contains enough memory to store the stack of digitized images that will be acquired while and as said system devices will operate to vary the image acquisition parameters over said range of values.

* * * * *

UNITED STATES PATENT AND TRADEMARK OFFICE
CERTIFICATE OF CORRECTION

PATENT NO.    : 6,724,419 B1
DATED         : April 20, 2004
INVENTOR(S)   : Daniel M. Green et al.

It is certified that error appears in the above-identified patent and that said Letters Patent is hereby corrected as shown below:

Column 3,
Line 33, "images so acqured images may" should read -- images so acquired may --

Column 9,
Lines 35, "manually directly" should read -- manually directing --

Signed and Sealed this

Twenty-eighth Day of December, 2004

JON W. DUDAS
*Director of the United States Patent and Trademark Office*